United States Patent [19]

Hansen, Jr. et al.

[11] Patent Number: 5,169,833
[45] Date of Patent: Dec. 8, 1992

[54] SUBSTITUTED CYCLIC PENTAPEPTIDES

[75] Inventors: Donald W. Hansen, Jr., Skokie; Sofya Tsymbalov, Des Plaines; Nizal S. Chandrakumar, Vernon Hills; Donna L. Hammond, Oak Park, all of Ill.; Henry I. Mosberg, Ann Arbor, Mich.

[73] Assignee: G. D. Searle & Co., Chicago, Ill.

[21] Appl. No.: 703,524

[22] Filed: May 21, 1991

Related U.S. Application Data

[63] Continuation-in-part of Ser. No. 497,833, Mar. 22, 1990, abandoned, which is a continuation-in-part of Ser. No. 451,290, Dec. 15, 1989, abandoned.

[51] Int. Cl.$^5$ .................. A61K 37/00; C07K 5/00
[52] U.S. Cl. .................. 514/17; 514/114 J; 514/809; 530/302; 530/330; 930/80
[58] Field of Search .................. 514/11, 17, 809; 530/302, 330; 930/80

[56] References Cited

U.S. PATENT DOCUMENTS

| | | | |
|---|---|---|---|
| 4,371,463 | 2/1983 | Pert et al. | 530/302 |
| 4,495,178 | 1/1985 | Hanser, Jr. et al. | 530/302 |
| 4,518,711 | 5/1985 | Hruby et al. | 514/11 |
| 4,760,180 | 7/1988 | Pitzele et al. | 564/157 |

FOREIGN PATENT DOCUMENTS 9000564 1/1990 World Int. Prop. O. .

OTHER PUBLICATIONS

Mosberg, et al., *Life Sciences*, 43 1013-1020 (1988).
Bradbury, et al., *Nature*, 260, 793 (1976).
Belluzzi, et al., *Nature*, 260, 625 (1976).
Kiso, et al., "Peptide Chemistry 1981," Protein Research Foundation, Osaka, Japan, 65-70 (1982).
Vavrek, et al., *Peptides*, 2, 303 (1981).
Mosberg, et al., Proc. Natl. Acad. Sci. USA, vol. 80, pp. 5871-5874, Oct. 1983.

*Primary Examiner*—Lester L. Lee
*Assistant Examiner*—B. Celsa
*Attorney, Agent, or Firm*—Roberta L. Hastreiter; Paul D. Matukaitis

[57] ABSTRACT

The present invention provides substituted cyclic pentapeptide compounds of general Formula I:

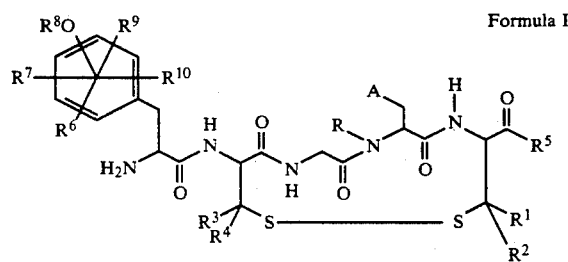

Formula I and the pharmaceutically-acceptable slats, esters and amides thereof, which are useful for inducing analgesia in animals, pharmaceutical compositions comprising a pharmaceutically-acceptable carrier and a compound of Formula I, and a method for inducing analgesia in an animal in need thereof comprising administering a therapeutically-effective amount of a compound of Formula I to the animal.

28 Claims, No Drawings

SUBSTITUTED CYCLIC PENTAPEPTIDES

The Government may have rights in the invention described herein pursuant to National Institute of Health Grant No. DA03910 awarded by the Department of Health and Human Services.

BACKGROUND OF THE INVENTION

1. Field of the Invention

This application is a continuation-in-part of application U.S. Ser. No. 497,833, filed on Mar. 22, 1990, entitled "Substituted Cyclic Penicillanic Acid Pentapeptides," now abandoned, which is a continuation-in-part of application U.S. Ser. No. 451,290, filed on Dec. 15, 1989, entitled "Substituted Cyclic Penicillanic Acid Pentapeptides," now abandoned.

The present invention provides novel compounds having pharmaceutical activity which are useful as pharmaceutical agents and, more particularly, as analgesic agents for the treatment of pain in animals, pharmaceutical compositions containing one or more of these compounds, methods of use employing these compounds and methods of manufacturing these compounds.

More specifically, the present invention concerns substituted cyclic pentapeptide compounds which, by apparently acting as neurotransmitters or neuromodulators in the central nervous pain-suppressant system, induce analgesia in animals, pharmaceutical compositions containing one or more of these compounds in combination with a pharmaceutically-acceptable carrier, and methods of treating pain employing these compounds.

Analgesic compounds are agents which alleviate pain without causing a loss of consciousness and, thus, which are useful for treating pain and, often, for reducing inflammation.

The major classes of analgesic compounds include analgesic-antipyretic compounds, compounds which alleviate pain and reduce fever, such as salicylates, and narcotic analgesics, or opiates, compounds which alleviate pain and induce sleep.

While salicylate and salicylate-like agents (non-steroidal antiinflammatory agents or NSAIDS) are efficacious in relieving pain, they often exhibit undesirable side effects, such as gastrointestinal irritation, including bleeding, as with aspirin, allergic response, as with aspirin, and/or liver toxicity with extended use, as with acetaminophen.

The compounds of the present invention are not salicylates, and represent another class of compounds which are useful as analgesic agents.

2. Description of the Related Art

Opioids are a class of drugs which are, to varying degrees, opium-like or morphine-like in their properties. Although opioids are employed therapeutically primarily as analgesics, they have many other pharmacological effects as well, and they have some of the properties of certain naturally-occurring peptides.

By the year 1967, researchers working in the art had concluded that the complex interactions in the body between morphine agonists (morphine-like drugs) and mixed morphine agonist-antagonists could best be explained by postulating the existence of more than one type of cellular receptor for the opioids, and for related drugs.

Subsequent research in the area revealed that multiple categories of opioid receptors exist and, further, that there are at least three distinct families of naturally-existing opioid peptides: (l) the endorphins; (2) the enkephalins; and (3) the dynorphins.

Although studies concerning the binding of opioid drugs and peptides to specific sites in the brain, and in other organs, have suggested the existence of, perhaps, as many as eight different types of opioid receptors in the body, there is reasonably firm evidence to support the conclusion that three major categories of opioid receptors, designated $\mu$, $\kappa$ and $\delta$, exist in the central nervous system. The classical opioid antagonist, naloxone, has been found to bind with high affinity to all three categories of opioid receptors.

The multiplicity of opioid receptor types in the central nervous system is now well established. Though much work has been directed at defining the structural elements that determine receptor specificity and efficacy, these factors are still, at best, poorly understood.

The rigid alkaloid opiates, typified by morphine, are generally believed to produce analgesia, as well as multiple adverse side effects, by interacting with the $\mu$ receptor.

It is now well established that the $\delta$ opioid receptor type mediates analgesia in the mouse, and that this site is associated with substantially fewer gastrointestinal transit effects, and with substantially less physical dependence, than the $\mu$ opioid receptor type.

In 1975, Hughes and Kosterlitz described the isolation of two naturally-occurring pentapeptides, "methionine enkephalin" ($H_2$N-Tyr-Gly-Gly-Phe-Met-OH) and "leucine enkephalin" ($H_2$N-Tyr-Gly-Gly-Phe-Leu-OH) from the brain. These pentapeptides occur in nerve endings of brain tissue, spinal cord and the gastrointestinal tract, bind to the same receptor sites as do the opiates, and exhibit some weak morphine-like actions, actions which were antagonized by naloxone.

That same year, Goldstein and his colleagues reported the presence of peptide-like substances in the pituitary gland which exhibited opioid activity.

The naturally-occurring pentapeptides isolated by Hughes and Kosterlitz appear to act as a neurotransmitters or neuromodulators in the central nervous system, and bind stereospecifically to partially-purified brain opiate receptor sites. See, for example, Bradbury et al., *Nature*, 260, 793 (1976). These natural peptides are also highly active in bioassays for opiate activity, but exhibit only weak, fleeting analgesic activity when injected directly into the brain of the rat, and exhibit no activity when administered systemically. See, for example, Belluzzi, et al., *Nature*, 260, 625 (1976).

In an attempt to overcome the lack of in vivo activity of the naturally-occurring pentapeptides isolated by Hughes and Kosterlitz, investigators working in the art have made numerous modifications to these enkephalins.

Among the modifications made to methionine enkephalin has been the synthesis of short-chain, enkephalin-like peptides, among them dipeptide and tripeptide alkylamides, as described by Kiso et al., "Peptide Chemistry 1981," Protein Research Foundation, Osaka, Japan, 65–70 (1982).

Vavrek et al., *Peptides*, 2, 303 (1981), disclose analogs of the enkephalins, including the dipeptide, tyrosine-D-alanine-phenylpropylamide.

The large-scale use of synthetic enkephalins has been impractical due to various difficulties. One of the difficulties associated with natural enkephalins is that they are extremely unstable, and their half-lives in the blood are extremely short.

Attempts at solving these problems focused upon altering the structure of the enkephalin molecule. Alterations in the enkephalin structure produce different pharmacological effects. To some degree, these effects are due to differential interactions with the various opioid receptors. However, it has been difficult to study the role of each receptor type, or to induce selectively the pharmacological and therapeutic effects associated with each receptor type, because the enkephalin analogs, to date, have had a high degree of selectivity for only the mu ($\mu$), rather than the delta ($\delta$), opioid receptors.

For several years, the prototypic agonist for the $\delta$ opioid receptor has been the cyclic enkephalin analog [D-Pen$^2$, D-Pens$^5$]enkephalin. The recently-discovered deltorphins, heptapeptides of frog skin origin, are also highly selective and potent, in vitro, at this receptor. However, the relatively large size of these peptides suggest potential problems in crossing the blood brain barrier to elicit analgesia after systemic administration, a desirable property for a useful opioid analgesic. This has also hampered attempts to more fully define the functional role of $\delta$ receptors in the central nervous system.

Compounds within the present invention are cyclic disulfide-bridged pentapeptide opioid agonists which have a substantial affinity for the $\delta$ opioid receptors, and which produce analgesia following central and peripheral routes of administration in animals.

The compounds of the present invention are structurally distinct from that which has been described in the art.

The compounds of the present invention bind preferentially to the delta ($\delta$) opioid brain receptors. Thus, this class of compounds would be expected to have different pharmacological profiles than peptide compounds which bind preferentially to the mu ($\mu$) opioid receptors of the brain.

Moreover, compounds of the present invention exhibit unexpected and surprisingly superior activities when compared to the di, tri, tetra and pentapeptides of the prior art. These novel pentapeptide derivatives show improved potency and bioavailability as analgesic agents by central and peripheral routes of administration, such as by subcutaneous administration.

H. I. Mosberg et al., in "Bis-Penicillamine Enkephalins Possess Highly Improved Specificity Toward Delta Opioid Receptors," *Proc. Natl. Acad. Sci. USA*, 80, 5871–5874 (1983), disclose cyclic pentapeptide compounds in which the tyrosine section of the compounds remains unsubstituted. Thus, the positions of the Mosberg et al. compounds which correspond to Variables $R^6$, $R^7$, $R^9$ and $R^{10}$ in Formula I, which is presented below in the "Summary of Invention" section, are each occupied by hydrogen atoms, not by alkyl radicals. Formula I, however, defines $R^6$, $R^7$, $R^9$ and $R^{10}$, four of the variables on the tyrosine section of the pentapeptide compounds of the invention described thereby, as independently being hydrogen or an alkyl radical, with the proviso that $R^6$, $R^7$, $R^9$ and $R^{10}$ are not each hydrogen. This is an important distinction between the pentapeptide compounds of the invention and the pentapeptide compounds described by Mosberg et al. As a result of this distinction, pentapeptide compounds described herein are unexpectedly superior to the pentapeptide compounds described by Mosberg et al.

SUMMARY OF THE INVENTION

The present invention provides compounds having a structure of Formula I:

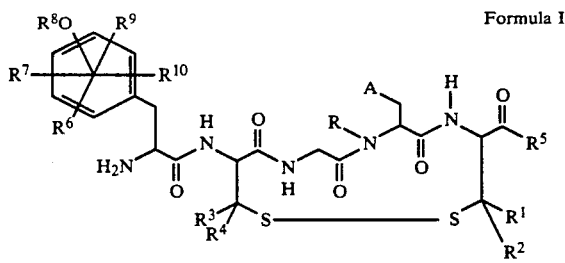

Formula I and the pharmaceutically-acceptable salts, esters and amides thereof, wherein:

A is: hydrogen,

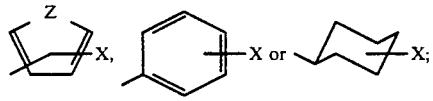

Z is: sulfur, nitrogen or oxygen;

X is: hydrogen, halogen, nitro, lower alkyl, lower alkyl substituted by halogen or nitro, aralkyl, alkaryl, or aralkyl or alkaryl substituted by hydrogen, halogen, nitro, lower alkyl or lower alkyl substituted by halogen or nitro;

R, $R^1$, $R^2$, $R^3$, $R^4$, $R^6$, $R^7$, $R^9$ and $R^{10}$ are: independently hydrogen or alkyl, with the proviso that $R^6$, $R^7$, $R^9$ and $R^{10}$ are not each hydrogen;

$R^5$ is: amino, hydroxy, alkoxy, alkylamino, dialkylamino or alkoxyaryl; and $R^8$ is: hydrogen, alkyl, alkyl carbonyl, alkoxy carbonyl, amino carbonyl, alkylaminocarbonyl or dialkylamino carbonyl, with any of the foregoing $R^8$ substituents being aryl substituted.

The present invention also provides pharmaceutical compositions which are pharmaceutically acceptable, and which comprise a therapeutically-effective amount of a compound of Formula I in combination with a pharmaceutically-acceptable carrier, and a method for eliminating or ameliorating pain in an animal comprising administering a therapeutically-effective amount of a compound of Formula I to the animal.

DETAILED DESCRIPTION OF THE INVENTION

Definitions

For purposes of clarity, the terms and phrases used throughout this specification and the appended claims are defined in the manner set forth directly below.

The term "alkyl" as used herein means a hydrocarbon radical having from one to ten carbon atoms, which can be a straight or branched chain, and including from zero to four carbon-carbon double or triple bonds. Representative of such radicals are methyl, ethyl, n-propyl, isopropyl, n-butyl, sec-butyl, isobutyl, tert-butyl, 2-ethylhexyl and the like.

The term "alkylamino" as used herein means an alkyl radical, as defined above, having an amino group as defined below, attached thereto.

The term "alkylaminocarbonyl" as used herein means an alkylamino radical, as defined above, having a carbonyl group, as defined below, attached thereto.

The term "alkylcarbonyl" as used herein means an alkyl radical, as defined above, having a carbonyl group, as defined below, attached thereto.

The term "alkaryl" as used herein means an alkyl radical, as defined above, having one or more hydrogen atoms replaced by an aryl radical, as defined below.

The term "alkoxy" as used herein means an alkyl radical, as defined above, having an oxygen atom attached thereto. Representative alkoxy groups include methoxy, ethoxy, propoxy, tert-butoxy and the like.

The term "alkoxyaryl" as used herein means an alkoxy radical, as defined above, including an aryl radical, as defined below.

The term "alkoxycarbonyl" as used herein means an alkoxy radical, as defined above, including a carbonyl group, as defined below.

The term "amino" as used herein means —NH$_2$.

The term "aminocarbonyl" as used herein means

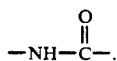

The term "analgesia" as used herein means the reduction, or absence, of sensibility to pain, designating particularly the relief of pain without loss of consciousness.

The term "animal" as used herein includes humans and animals.

The term "aryl" as used herein means 5- and 6-membered single-ring aromatic radicals which may include from zero to four heteroatoms, for example, phenyl, thienyl, furanyl, pyridinyl, imidazolyl, pyrimidyl, (is-)oxazolyl, thiazolyl, triazolyl, tetrazolyl, pyrrolyl and the like.

The term "aralkyl" as used herein means an aryl radical, as defined above, having one or more hydrogen atoms replaced by an alkyl radical, as defined above, for example, N-methylpyrrolyl.

The term "benzyl" as used herein means C$_6$H$_5$CH$_2$—.

The phrase "blood brain barrier" as used herein means a chemical barrier made up by the cell walls of the capillaries which are present in the brain tissues, through which drugs circulating in the blood must pass in order to have an effect in the central nervous system.

The abbreviation "Bzl" as used herein means benzyl.

The abbreviation "Boc" as used herein means t-butyloxycarbonyl.

The term "carbonyl" as used herein means

The term "carboxyl" as used herein means

The term "composition" as used herein means a product which results from the combining of more than one element or ingredient.

The term "dialkylaminocarbonyl" as used herein means

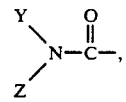

wherein Y and Z are each independently alkyl, as defined above.

The term "dialkylamino" as used herein means

wherein Y and Z are each independently alkyl, as defined above.

The abbreviation "DCC" as used herein means dicyclohexylcarbodiimide.

The abbreviation "DIEA" as used herein means diisopropylethylamine.

The abbreviation "DMF" as used herein means dimethylformamide.

The phrase "ED$_{50}$ value" as used herein means that dose of a compound or drug which produced a biological effect, such as producing analgesia, in 50% of the animals to which the compound or drug was administered.

The abbreviation "Et" as used herein means ethyl (—CH$_2$CH$_3$).

The abbreviation "EtOH" as used herein means ethanol (CH$_3$CH$_2$OH).

The term "halo" or "halogen" as used herein means chlorine (Cl), bromine (Br), fluorine (F) and/or iodine (I).

The term "heteroatom" as used herein means an atom of any element other than carbon or hydrogen.

The abbreviation "HOBT" as used herein means 1-hydroxybenzotriazole.

The term "hydroxy" as used herein means —OH.

The abbreviation "i.c.v." as used herein means that a compound or drug was administered intracerebroventricularly.

The term "intracerebroventricularly" as used herein means that a compound or drug was administered into the brain.

The abbreviation "i.g." as used herein means that a compound or drug was administered intragastrically.

The term "intragastrically" as used herein means that a compound or drug was administered into the stomach.

The abbreviation "i.p." as used herein means that a compound or drug was administered intraperitoneally.

The term "intraperitoneally" as used herein means that a compound or drug was administered through the peritoneum (the membrane lining the abdominopelvic walls and investing the viscera).

The term "lower alkyl" as used herein means an alkyl radical, as defined above, but having from one to six carbon atoms, rather than from one to ten carbon atoms.

The abbreviation "Me" as used herein means methyl (—CH$_3$).

The abbreviation "MeOH" as used herein means methanol (CH$_3$OH).

The phrase "methyl ester" as used herein means

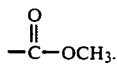

The acronym "NSAID" as used herein means nonsteroidal antiinflammatory drug, as discussed by J. G. Lombardino, Ed. *Nonsteroidal Antiinflammatory Drugs, Chemistry and Pharmacology of Drug Series*, Wiley, N.Y. (1985).

The term "nitro" as used herein means —$NO_2$.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, as defined directly above, such as a liquid or solid filler, diluent, excipient, solvent or encapsulating material, involved in carrying or transporting a chemical compound or pharmaceutical agent from one organ, or portion of the body, to another organ, or portion of the body. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The phrase "pharmaceutically-acceptable salts" as used herein refers to non-toxic salts of the compounds of the present invention which are generally prepared by reacting the free base with a suitable organic or inorganic acid, or which are prepared by reacting the free acid with a suitable base. Representative salts include the hydrochloride, hydrobromide, sulfate, bisulfate, acetate, oxalate, valerate, oleate, palmitate, stearate, laurate, borate, benzoate, lactate, phosphate, tosylate, citrate, maleate, fumarate, succinate, tartrate, napsylate, clavulanate and the like salts and alkali metal salts, such as sodium and potassium, and alkaline earth salts, such as calcium and magnesium.

The abbreviation "Ph" as used herein means phenyl, as defined below.

The term "phenyl" as used herein means the group $C_6H_5$—, derived from benzene.

The abbreviation "p.o." as used herein means that a compound or drug was administered orally.

The phrase "protecting group" as used herein means substituents which protect the reactive functional group from undesirable chemical reactions. Examples of such protecting groups include esters of carboxylic acids, ethers of alcohols and acetals and ketals of aldehydes and ketones.

The phrase "N-protecting group" or "N-protected" as used herein means those groups intended to protect the N-terminus of an amino acid or peptide, to protect an amino group against undesirable reactions during synthetic procedures and includes, but is not limited to, sulfonyl, acyl, acetyl, pivaloyl, t-butyloxycarbonyl (Boc), carbonylbenzyloxy (Cbz), benzoyl and an L- or D-aminoacyl residue, which may itself be N-protected similarly.

The abbreviation "RaNi" as used herein means Raney nickel.

The abbreviation "s.c." as used herein means that a compound or drug was administered subcutaneously.

The phrase "solid-phase resin" as used herein means a solid or semi solid substance which has been functionalized, for example, Merrifield and PMBHA resins.

The phrases "systemic administration" and "peripheral administration" as used herein mean the administration of a compound, drug or other material other than directly into the central nervous system, such that it enters the patient's system and, thus, is subject to metabolism and other like processes, for example, subcutaneous administration.

The abbreviation "TFA" as used herein means trifluoroacetic.

The phrase "therapeutically-effective amount" as used herein means that amount of a compound, material, or composition which is effective for eliminating or ameliorating pain in an animal, or for producing some other desired therapeutic effect, at a reasonable benefit/risk ratio applicable to any medical treatment.

The abbreviation "THF" as used herein means tetrahydrofuran.

The phrases "title compound," "title product," "title peptide" and "title material" as used herein mean that compound, peptide or material whose chemical name is given, and whose structure is shown, in the particular example referred to. If no particular example is referred to, it means that compound, peptide or material whose chemical name is given, and whose structure is shown, in the particular example in which it appears.

Amino acid sequences appearing herein may be identified according to the following three-letter abbreviations.

| Amino Acid | Three-Letter Abbreviation |
|---|---|
| Alanine | Ala |
| Arginine | Arg |
| Asparagine | Asn |
| Aspartic Acid | Asp |
| Cysteine | Cys |
| Glutamine | Gln |
| Glutamic Acid | Glu |
| Histidine | His |
| Isoleucine | Ile |
| Leucine | Leu |

-continued

| Amino Acid | Three-Letter Abbreviation |
|---|---|
| Lysine | Lys |
| Methionine | Met |
| Penicillamine | Pen |
| Phenylalanine | Phe |
| Proline | Pro |
| Serine | Ser |
| Threonine | Thr |
| Tryptophan | Trp |
| Tyrosine | Tyr |
| Valine | Val |

The letters "L" and "D" appearing herein indicate whether a particular amino acid is levorotatory (L) or dextrorotatory (D). Unless otherwise indicated, the amino acids appearing herein are L-enantiomorphs (levorotatory), rather than D-enantiomorphs (dextrorotatory).

A superscript number which appears to the right of an amino acid name or three-letter abbreviation indicates the position of the particular amino acid in the sequence of amino acids, reading the sequence from left to right (from the N-terminus). For example, $Phe^4$ indicates that phenylalanine is in the fourth position of the sequence from the N-terminus.

Some of the chemical structures which are presented in this specification and the appended claims have been drawn using the convention which employs lines to represent alkyl radicals, which is known by those of skill in the art.

Description of Invention

In one aspect, the present invention provides compounds comprising a structure of Formula I, as described above in the "Summary of Invention" section, which are pharmaceutically acceptable, and pharmaceutically-acceptable salts, esters and amides thereof.

The compounds of the present invention comprise a class of substituted cyclic pentapeptide compounds. Preferred compounds of the present invention are those in which the $R^6$ and $R^7$ positions thereof, as shown in Formula I, are each substituted by methyl. The most preferred compound of the present invention is the pentapeptide shown and described in Example 4.

Specific compounds contemplated as falling within the scope of the invention include, but are not limited to, the compounds discussed in the examples presented below, as well as their pharmaceutically-acceptable salts, esters, and amides.

Contemplated equivalents of the compounds described in Formula I include compounds which otherwise correspond thereto, and which have the same general properties thereof, wherein one or more simple variations of substituents are made which do not adversely affect the efficacy of the compound.

Certain compounds of this invention may exist in geometric or stereoisomeric forms. The present invention contemplates all such compounds, including cis- and transgeometric isomers, R- and S-enantiomers, diastereomers, d-isomers, isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention.

Certain compounds of the present invention may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ during the final isolation and purification of the compounds of the invention, or by separately reacting a purified compound of the invention in its free base form with a suitable organic or inorganic acid, and isolating the salt thus formed. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, S. M. Berge et al., "Pharmaceutical Salts," *J. Pharm. Sci.*, 66:1–19 (1977).)

In other cases, the compounds of the invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ during the final isolation and purification of the compounds, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, S. M. Berge et al., "Pharmaceutical Salts," supra.)

In another aspect, the present invention provides pharmaceutically-acceptable compositions which comprise a therapeutically-effective amount of one or more of the compounds of Formula I, as described hereinabove, formulated together with one or more pharmaceutically-acceptable carriers. As described in detail below, the pharmaceutical compositions of the present invention may be specially formulated for oral administration in solid or liquid form, for parenteral injection, or for rectal or vaginal administration.

In yet a further aspect, the present invention provides a method for eliminating or ameliorating pain in an animal comprising administering a therapeutically-effective amount of a compound of Formula I, as described hereinabove, to the animal.

Utility

By virtue of their analgesic activity, the compounds of the present invention, and the pharmaceutical compositions comprising one or more of these compounds, are useful as analgesic agents for the elimination or amelioration of pain in animals.

Methods of Preparation

In general, the compounds of the present invention may be prepared by the methods illustrated in the following general reaction schemes, or by modifications thereof, using readily available starting materials, reagents and conventional synthesis procedures. In these reactions, it is also possible to make use of variants which are in themselves known, but are not mentioned here.

Unless otherwise specified, the various substituents of the compounds shown in the general reaction schemes are defined in the same manner as they are defined above in Formula I in the "Summary of Invention" section.

If a particular enantiomer of a compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

General Reaction Scheme No. 1 describes the solid phase synthesis of the pentapeptides of Formula I. The C-terminal amino acid is attached to the polymer resin, and each successive amino acid is added to the N-terminus of the resin-bound peptide. The completed protected linear peptide is removed from the resin and cyclized to provide the compounds of this invention.

General Reaction Scheme No. 2 describes a solution synthesis of the pentapeptides of Formula I. The cyclization step is carried out at the tetrapeptide stage, which lacks the tyrosine (Tyr) unit in the one position. This cyclic peptide fragment is deprotected and coupled to the N-terminal Tyr to generate the products of this invention after final deprotection.

General Reaction Scheme No. 3 describes an alternative solution synthesis of the pentapeptides of Formula I. The cyclization step and final product generation are also carried out from the same tetra-peptide illustrated in Scheme No. 2. The cyclization precursor is synthesized by coupling N-protected amino acid two successively with glycine methyl ester, amino acid four, and the C-terminal amino acid.

GENERAL REACTION SCHEME NO. 1

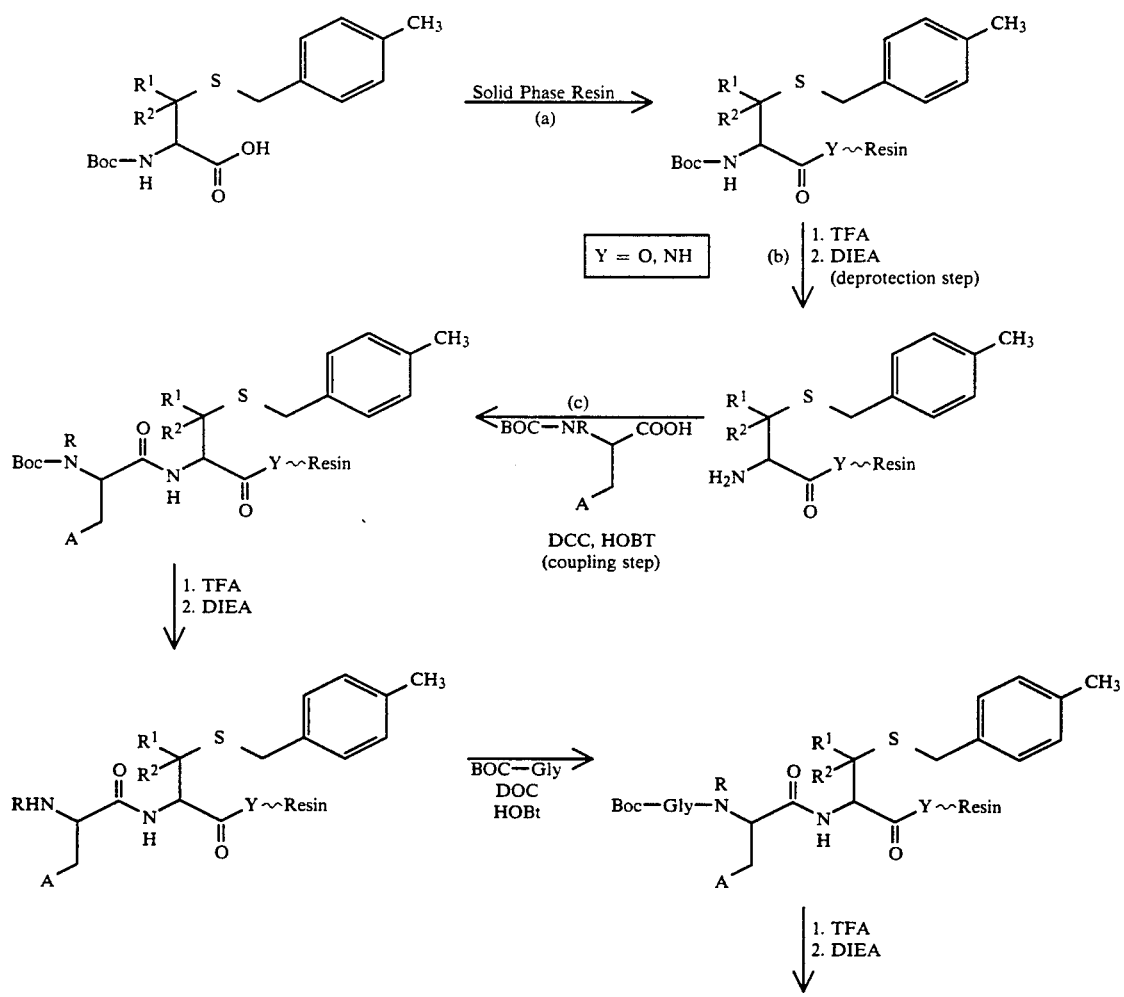

5,169,833
-continued
GENERAL REACTION SCHEME NO. 1
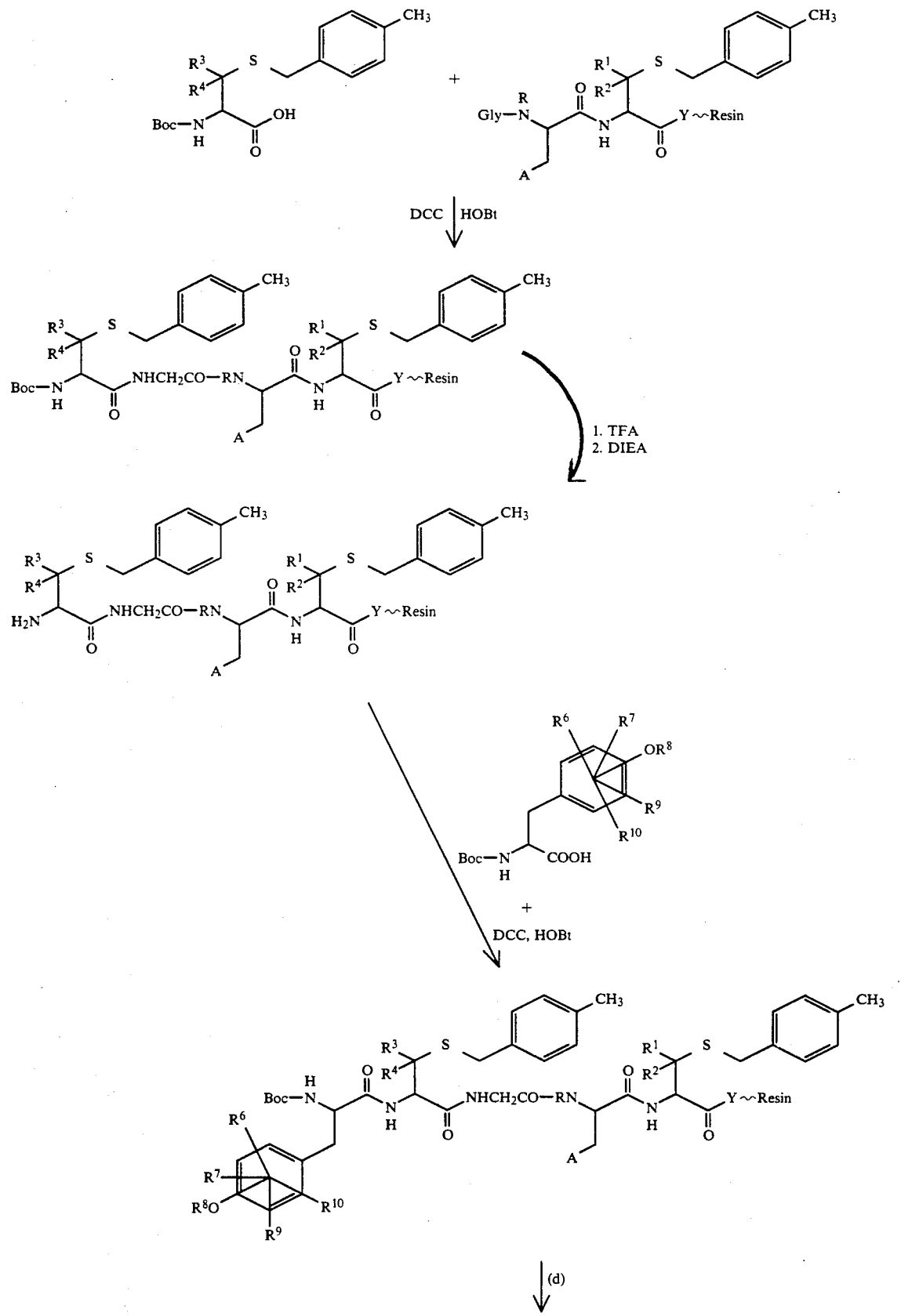

-continued
GENERAL REACTION SCHEME NO. 1

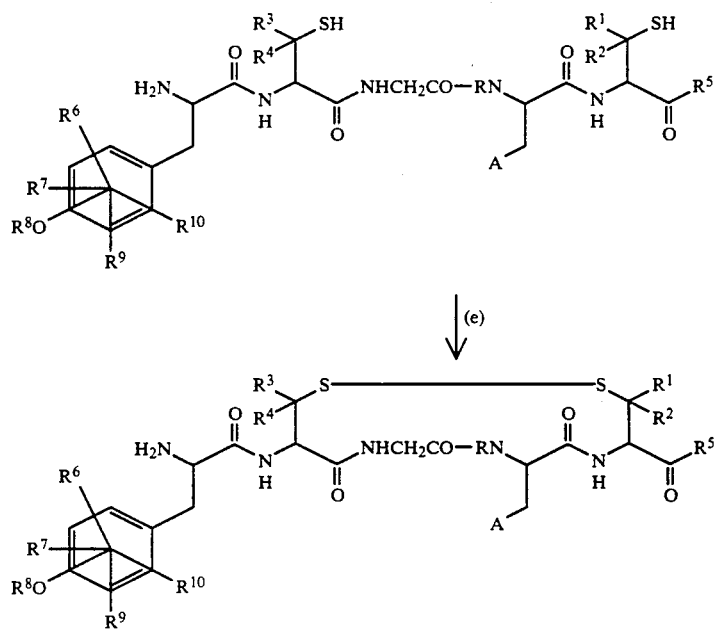

The following letters correspond to the same letters employed in General Reaction Scheme No. 1:

(a) For the carboxy terminal carboxylic acid of the final peptide, $R^5$ represents OH. Merrifield resin is used. Attachment of the compound to the resin is via an ester formed via intermediate CS salt. For carboxy terminal carboxamide of the final peptide, $R^5$ represents $NH_2$. P-methylbenzhydrylamine (pMBHA) resin is used, and linkage of the compound to the resin is via amide.

(b) The complete protocol for the deprotection and washing steps is included separately below.

(c) The complete protocol for the coupling step is included separately below, as the "Solid Phase Peptide Synthesis Coupling Methodology for Chain Elongation of Resin Bound Peptide."

(d) For both the Merrifield and the PMBHA resins, cleavage of peptide from resin is effected by treatment with hydrofluoric acid (HF). In the former case, an unprotected, C-terminal carboxylic acid-containing peptide is afforded. In the latter case, an unprotected, C-terminal carboxamide-containing peptide results.

(e) Cyclization is achieved by treatment with $K_3Fe(CN)_6$ at a pH of from about 7.5 to about 8.5.

GENERAL REACTION SCHEME NO. 2

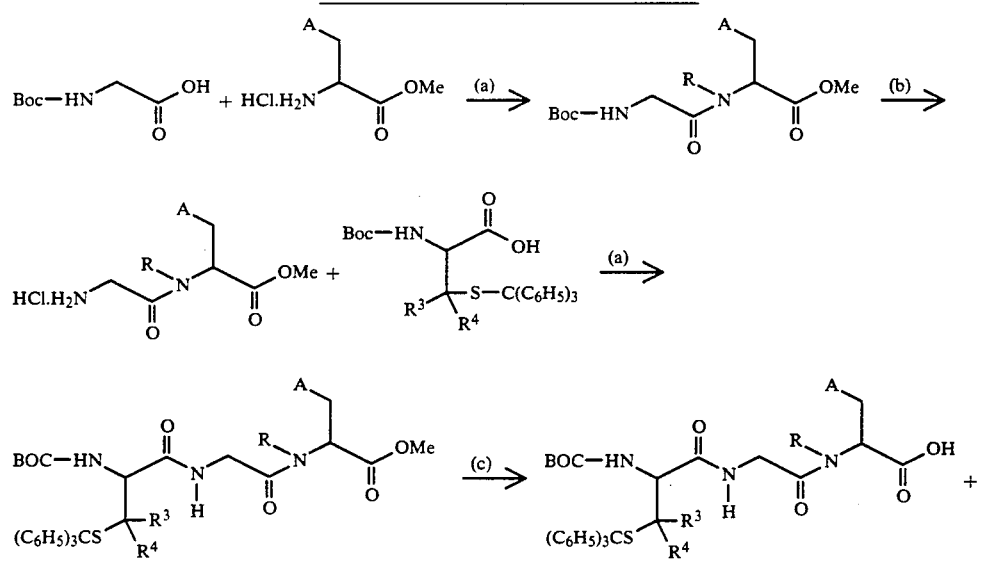

-continued
GENERAL REACTION SCHEME NO. 2
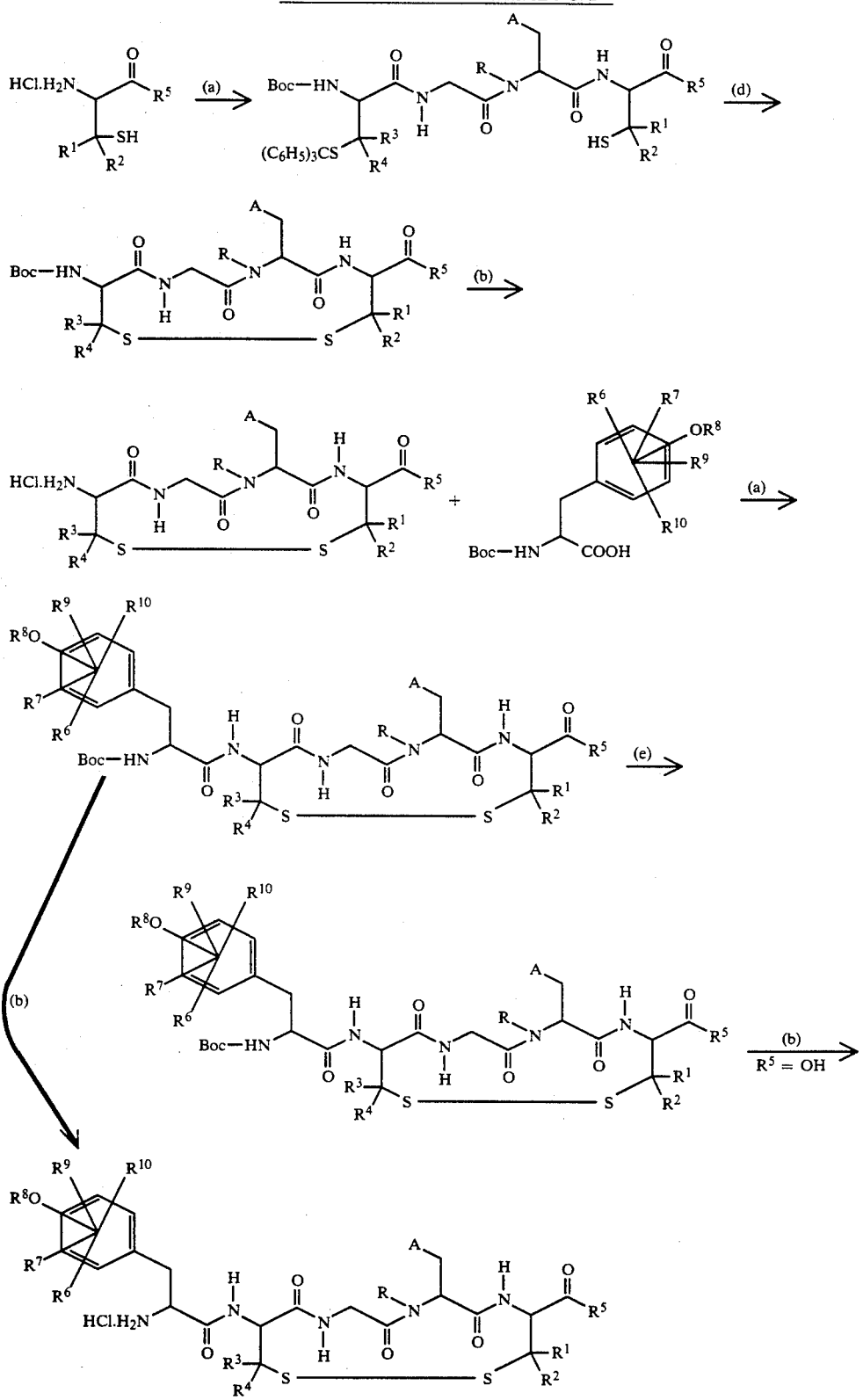
The following letters correspond to the same letters employed in General Reaction Scheme No. 2:
(a) Isobutylchloroformate (IBCF), N-methylmorpholine (NMM), $CH_2Cl_2$.
(b) Hydrochloric acid (HCl), dioxane, Acetic acid (HOAc).
(c) Methanol (MeOH), sodium hydroxide (NaOH).
(d) Iodine ($I_2$), acetic acid (HOAc), water or $CH_2Cl_2$.

(e) Lithium hydroxide (LiOH), tetrahydrofuran (THF).
GENERAL REACTION SCHEME NO. 3
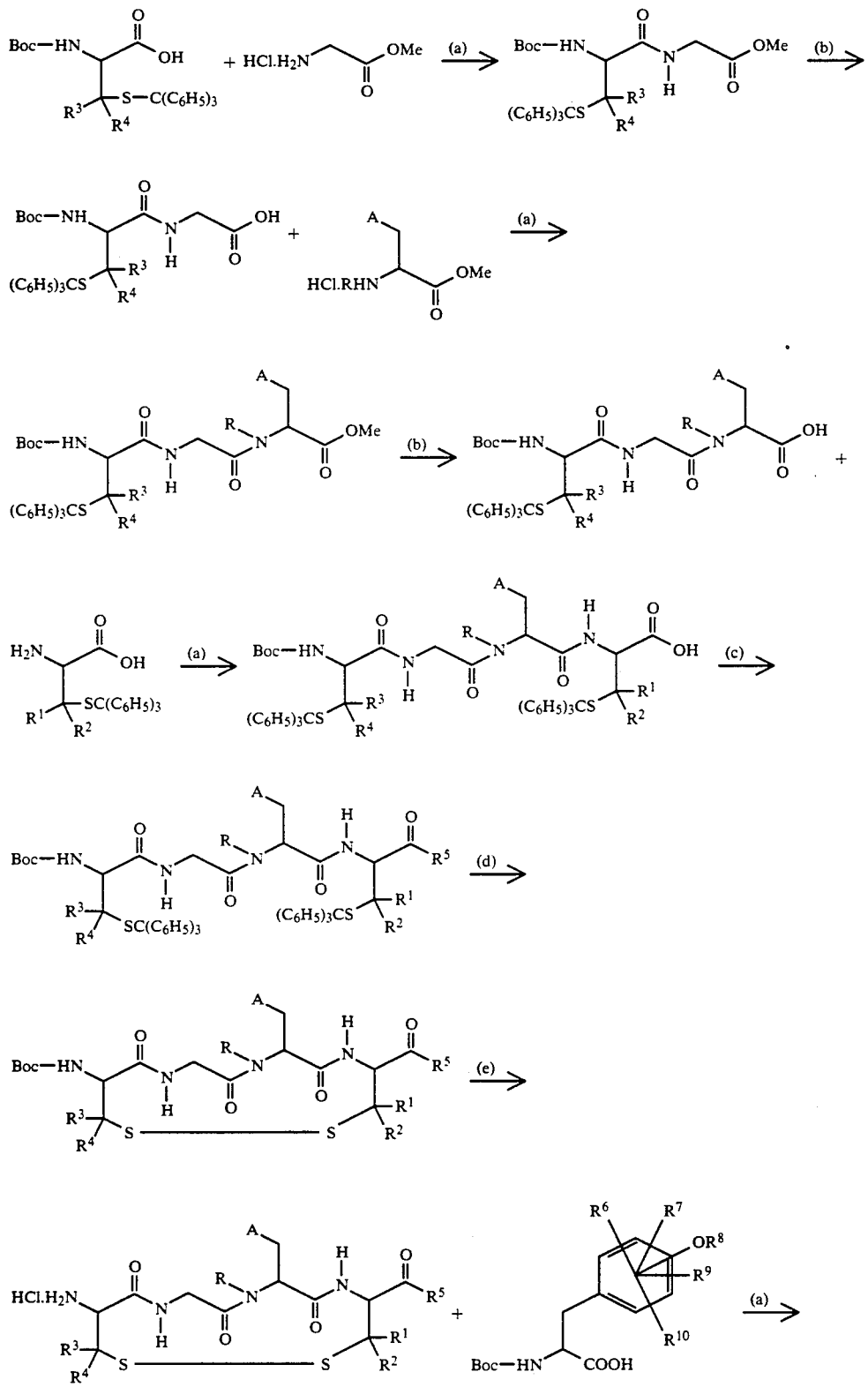

-continued
GENERAL REACTION SCHEME NO. 3

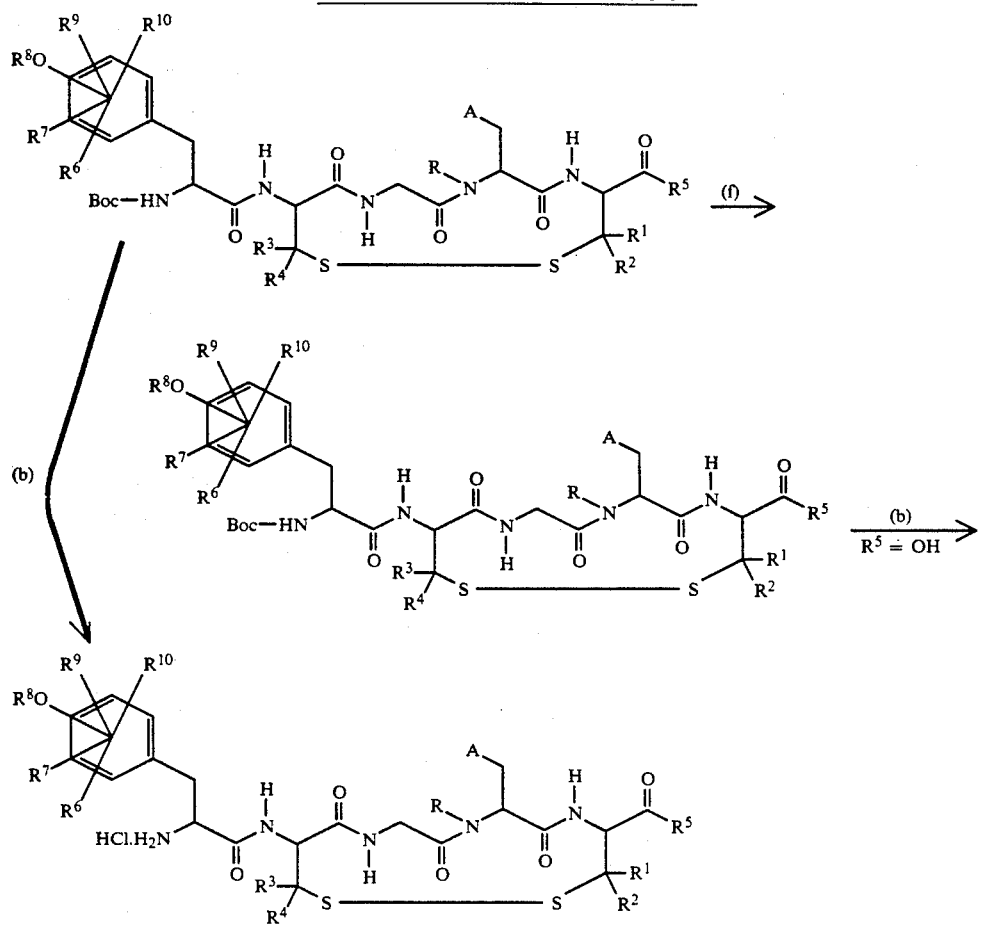

The following letters correspond to the same letters employed in General Reaction Scheme No. 3:

(a) Dimethylformamide (DMF), 1-hydroxybenzotriazole hydrate (HOBT), 1-(3-dimethylaminopropyl)3-ethylcarbodiimide hydrochloride, N-methylmorpholine (NMM).

(b) Methanol (MeOH), sodium hydroxide (NaOH).

(c) $Cs_2CO_3$, MeOH, DMF, $R^5$-Bromide.

(d) Iodine ($I_2$), acetic acid (HOAc), water or methylene chloride.

(e) Hydrochloric acid (HCl), dioxane, HOAc.

| | Solid Phase Peptide Synthesis Coupling Methodology for Chain Elongation of Resin Bound Peptide | | |
|---|---|---|---|
| Step | Reagent | Duration (Minutes) | Number of Times |
| 1 | $CH_2Cl_2$ | 2 | 4 |
| 2 | $TFA/CH_2Cl_2$(1:1) | 2 | 1 |
| 3 | $TFA/CH_2Cl_2$(1:1) | 20 | 1 |
| 4 | $CH_2CH_2$ | 2 | 3 |
| 5 | $DIEA/CH_2Cl_2$(1:9) | 2 | 2 |
| 6* | $CH_2Cl_2$ | 2 | 4 |
| 7[a] | Boc-Amino Acid/$CH_2Cl_2$ | 5 | 1 |
| 8[b] | DCC—$CH_2Cl_2$ + HOBT—DMT | 120 | 1 |
| 9 | $CH_2Cl_2$ | 2 | 3 |
| 10 | EtOH | 2 | 3 |
| 11* | $CH_2Cl_2$ | 2 | 4 |

[a]Boc amino acids used at 3 moles/mole of resin-bound peptide.
[b]DCC and HOBT added at 0.8 mole/mole of Boc amino acid.
*Ninhydrin tests are run after Step 6, and after Step 11. A positive result after Step 6, and a negative result after Step 11, are required before continuation.

The conditions for carrying out the individual steps in each of the general reaction schemes presented above are conventional, well-known, and capable of wide variation.

Other methods known in the art can also be used to synthesize the compounds of the present invention.

Dosage and Mode of Administration

The compounds of the present invention, and the pharmaceutical compositions comprising one or more of these compounds in combination with a pharmaceutically-acceptable carrier, are useful for treating pain in animals. A physician or veterinarian of ordinary skill in the art can readily determine whether or not a patient is in pain.

The pharmaceutical compositions of the present invention, which will typically comprise one or more of the compounds of Formula I, as described in the "Summary of Invention" section, as an active ingredient in admixture with one or more pharmaceutically-acceptable carriers and, optionally, with one or more other compounds, drugs or materials, are employed therapeutically and, thus, would generally be used under the guidance of a physician. The appropriate dosage and form of administration of these compositions will be suitably selected by methods which are consistent with conventional pharmaceutical practices.

The pharmaceutical compositions of the present invention may be specially formulated for oral administration in solid or liquid form, for parenteral injection, and/or for rectal or vaginal administration. These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually. While the preferred routes of administration are intravenous, intracerebroventricular and subcutaneous, the most preferred modes of administration are intravenous and subcutaneous.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the severity of the pain, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required to alleviate or ameliorate a particular patient's pain. For example, the physician or veterinarian could start doses of the compound of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous, intracerebroventricular and subcutaneous doses of the compounds of this invention for a patient, when used for the indicated analgesic effects, will range from about 0.0001 to about 100 mg per kilogram of body weight per day. If desired, the effective daily dose of the active compound may be administered as two, three, four, five, six or more sub-doses administered separately at appropriate intervals throughout the day, optionally, in unit dosage forms.

While it is possible for a compound of the present invention to be administered alone, it is preferable to administer the compound as a pharmaceutical formulation (composition).

The pharmaceutical compositions of the present invention comprise a compound of the present invention together with one or more pharmaceutically-acceptable carriers thereof and, optionally, with other therapeutic agents. Each carrier must be "acceptable" in the sense of being compatible with the other ingredients of the formulation and not injurious to the patient.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient (compound of Formula I) which can be combined with a carrier material to produce a single dosage form will vary depending upon the host being treated, the particular mode of administration and all of the other factors described above. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, with one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient (compound of Formula I) is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient (compound of Formula I), the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Opthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the drug in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The injectable materials can be sterilized, for example, by filtration through a bacterial-retaining filter, or by incorporating sterilizing agents in the form of sterile solid compositions which can be dissolved or dispersed in sterile water or in other sterile injectable mediums just prior to use.

The formulations may be presented in unit-dose or multi-dose sealed containers, for example, ampoules and vials, and may be stored in a lyophilized condition requiring only the addition of the sterile liquid carrier, for example water for injections, immediately prior to use. Extemporaneous injection solutions and suspensions may be prepared from sterile powders, granules and tablets of the type described above.

The pharmaceutical compositions of the present invention may also be used in the form of veterinary formulations, including those adapted for the following: (1) oral administration, for example, drenches (aqueous or non-aqueous solutions or suspensions), tablets, boluses, powders, granules or pellets for admixture with feed stuffs, pastes for application to the tongue; (2) parenteral administration, for example, by subcutaneous, intramuscular or intravenous injection as, for example, a sterile solution or suspension or, when appropriate, by intramammary injection where a suspension or solution is introduced into the udder of the animal via its teat; (3) topical application, for example, as a cream, ointment or spray applied to the skin; or (4) intravaginally, for example, as a pessary, cream or foam.

While the various aspects of the present invention are described herein with some particularity, those of skill in the art will recognize numerous modifications and variations which remain within the spirit of the invention. These modifications and variations are within the scope of the invention as described and claimed herein.

Examples

The following non-limiting examples describe and illustrate the methods for the preparation of the compounds of the present invention, as well as other aspects of the present invention, and the results achieved thereby, in further detail. Both an explanation of, and the actual procedures for, the various aspects of the present invention are described where appropriate. These examples are intended to be merely illustrative of the present invention, and not limiting thereof in either scope or spirit. Those of skill in the art will readily understand that known variations of the conditions and processes of the preparative procedures described in these examples can be used to prepare the compounds of the present invention, and the pharmaceutical compositions comprising such compounds.

All patents and publications referred to in the examples, and throughout the specification, are hereby incorporated herein by reference, without admission that such is prior art.

In the examples, all parts are by weight, and all temperatures are degrees Celsius, unless otherwise noted. Unless otherwise noted, Infrared (IR) and Nuclear Magnetic Resonance (NMR) spectra were consistent with the assigned structure.

All starting materials used in the examples are commercially available, and were obtained from Aldrich Chemical Co. (Milwaukee, Wis.), Bachem Bioscience Inc. (Philadelphia, Pa.), Chemical Dynamics Corp. (South Plainfield, N.J.), Sigma Chemical Co. (St. Louis, Mo.) and/or Peptides International (Louisville, Ky.).

While Examples 1-3 describe four different assays which were conducted with compounds of the present invention, Examples 4-42 describe specific methods for synthesis of compounds within the present invention.

Examples 1 (Writhing Assay) and 2 (Tail Flick and Hot Plate Assays) describe experiments which were conducted to compare the analgesic activity of several pentapeptide compounds described herein with a pentapeptide compound described by Mosberg et al., supra., designated "the Mosberg Pentapeptide," in different analgesic assays, as described in detail hereinbelow.

The structure of the Mosberg Pentapeptide is shown below.

The synthesis of Test Pentapeptide Nos. 1-5 are described in the examples which correspond thereto, as indicated below.

Peptide Structures

Mosberg Pentapeptide

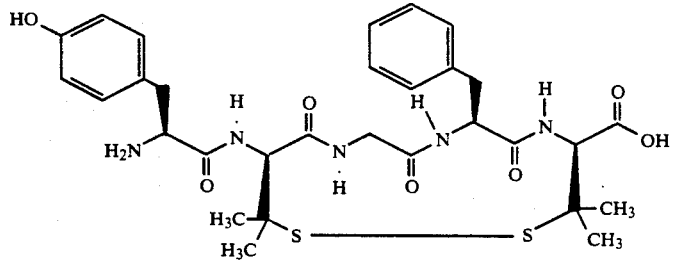

| Test Pentapeptide No. | Example No. |
|---|---|
| Test Pentapeptide No. 1 | Example 4 |
| Test Pentapeptide No. 2 | Example 16 |
| Test Pentapeptide No. 3 | Example 23 |
| Test Pentapeptide No. 4 | Example 24 |
| Test Pentapeptide No. 5 | Example 41 |

Test Pentapeptide Nos. 1-5 above were each tested in one or more of the following three analgesic assays, as described in Examples 1 and 2 below: (1) the Writhing Assay; (2) the Tail Flick Assay; and/or (3) the Hot Plate Assay. These assays were performed in the manner described in Examples 1 and 2 below. These pentapeptides, as well as the Mosberg Pentapeptide, were administered to the mice and/or rats employed in these assays subcutaneously, intracerebroventricularly and/or intragastrically, as indicated in the tables of data presented in Examples 1 and 2 below.

EXAMPLE 1

Writhing Assay

The "Writhing Assay" is one of the most widely-used experimental procedures for measuring the analgesic activity of different narcotic and nonnarcotic analgesic agents, and involves the continuous, chemically-induced pain of visceral origin to an animal, such as a mouse or rat. [Gyires et al., *Arch. int. Pharmacodyn*, 267, 131-140 (1984); C. Vander Wende et al., *Fed. Proc.*, 15, 494 (1956); Koster et al., *Fed. Proc.*, 18, 412 (1959); and Witken et al., *J. Pharmacol. Exp. Ther.*, 133, 400-408 (1961).] Chemicals which may be used to induce this pain include phenylbenzoquinone (PBQ) and acetic acid. As a result of the chemical irritation to the animal, a characteristic stretching and writhing of the animal (dorsiflexion of the animal's back, extension of its hindlimbs and the strong contraction of its abdominal musculature) will generally occur. The intensity of this pain reaction is determined by the number of writhes exhibited by the animal during a given period of time. Drugs which reduce the number of writhes of the animal appear to restore the normal nociceptive threshold of the animal.

Compounds of the present invention exhibit analgesic activity in mice, as shown by the results of the Writhing Assay presented in Table I below.

This assay was conducted generally in the manner described by R. I. Taber, "Predictive Value of Analgesic Assays in Mice and Rats," *Advances in Biochemical Psychopharmacology*, 8, 191 (1974).

Two hundred CD Charles River mice, weighing 20 to 30 grams were used in this assay.

Twenty-five minutes after subcutaneous administration, and fifteen minutes after intragastric administration, to the mice of 10 mg per kilogram (mpk) of body weight of either a Test Pentapeptide or the Mosberg Pentapeptide, 0.1 ml per 10 g of body weight of a 0.025% w/v solution of PBQ was injected intraperitoneally into each mouse. Some mice were given saline in place of a Test Pentapeptide, or the Mosberg Pentapeptide, and were used as a control group.

Five minutes later, each mouse was individually placed into a glass beaker for observation, and the number of writhes occurring during the following ten-minute period was counted.

A pentapeptide compound was considered to be "active" (to have produced analgesia in a mouse) if, after the administration of 10 mg per kilogram (mpk) of body weight of the compound to the mouse, the number of writhes elicited by a mouse injected with PBQ was equal to, or less than, one-half the median number of writhes recorded for the saline-treated control group of mice that day, as described by R. I. Taber, supra.

The standard initial screening dose of a test compound employed in this assay was 10 mpk per gram of body weight for both routes of administration. If this initial screening dose of the test compound produced analgesia in seven of ten mice, then the effect of additional doses of the test compound on the writhing response was evaluated, and then the $ED_{50}$ value (that dose of a compound which produced analgesia in 50% of the mice to which the compound was administered) was generally calculated. A maximum likelihood function was used to determine the $ED_{50}$ value. (The slopes of the dose-response curves for all test compounds analyzed were compared as described by Tallarida and Murray, *Manual of Pharmacologic Calculations*, Page 11 (Springer Verlag, New York, 1981)).

The results for the peptides analyzed in this assay, and discussed in the examples which correspond thereto, are presented in Table I below, and are expressed in terms of either the number of mice out of ten in which a peptide was considered to be "active" (a number which is a fraction) or the $ED_{50}$ value (a number which is not a fraction).

As Table I shows, the rank order of potency of the more potent compounds of the present invention tested in the Writhing Assay was: Test Pentapeptide No. 3 (Example 23)>Test Pentapeptide No. 2 (Example 26)>Test Pentapeptide No. 1 (Example 4). Thus, the peptide shown and synthesized in Example 23 was determined to be the most potent compound of the invention tested in the Writhing Assay, and is a preferred compound of the invention.

The Mosberg Pentapeptide was determined to be inactive in the Writhing Assay by both routes of administration at 30 mpk.

TABLE I

Data Generated from the Writhing Assay

| Peptide Tested | Subcutaneous | Intragastric | Example Number |
|---|---|---|---|
| Test Pentapeptide No. 1 | 2.6 mpk | 3/10 | 4 |
| Test Pentapeptide No. 2 | 2.1 mpk | 3/10 | 16 |
| Test Pentapeptide No. 5 | 3/10 | 4/10 | 41 |
| Test Pentapeptide No. 3 | 1.9 mpk | 4/10 | 23 |
| Test Pentapeptide No. 4 | 2/10 | 2/10 | 24 |
| Mosberg Pentapeptide | Inactive at 30 mpk | Inactive at 30 mpk | None |

EXAMPLE 2

Tail Flick and Hot Plate Assays

The "Tail Flick Assay" and the "Hot Plate Assay" (also known as the "Hind Paw Lick Assay") use thermal pain of transient duration, and are tests in which the pain threshold of the mice or rats being analyzed has not been altered. They are useful for evaluating the ability of a compound or drug to increase the animal's pain threshold (i.e. prolong response latencies), rather than to restore normal thresholds.

The heat-induced response to the Tail Flick Assay is a reflex reaction mediated at the level of the spinal cord. The heat-induced response to the Hot Plate Assay, however, is a more complex behavior requiring integration at higher centers in the brain.

When used together, the Tail Flick Assay and Hot Plate Assay provide two different methods of concurrently measuring analgesia in an animal. Compounds which are active in one of the assays may not be active in the other assay.

Opiate compounds having clinical efficacy as analgesics generally increase tail flick and/or hot plate latencies. Thus, morphine and codeine are generally determined to be active in both of these tests. In contrast, aspirin and Zomax, which are Non-Steroidal Antiinflammatory Drugs (NSAIDs), show little activity in either of these tests. However, these tests are not sufficiently sensitive, or of the appropriate design, to demonstrate the analgesic activity of NSAIDs.

The Tail Flick Assay and the Hot Plate Assay were performed generally in the manner described by G. Woolfe et al., "The Evaluation of the Analgesic Action of Pethidine Hydrochloride (Demerol)," *J. Pharmacol. Exp. Ther.*, 80, 300, (1944), F. D'Amour et al., "A Method for Determining Loss of Pain Sensation," *J. Pharmacol. Exp. Ther.*, 72, 74, 300-307 (1941), and E. Drower et al., "The Antinociceptive Effects of Prostaglandin Antagonists in the Rat," *European Journal of Pharmacology*, 133, 249-256 (1987).

Male Charles River albino mice and male Charles River Sprague-Dawley rats weighing 20 to 30 g, and 200 to 250 g, respectively, were employed in these assays.

Tail flick response latencies (defined as the time that elapsed between the onset of a high intensity beam of light and the reflex removal of the mouse or rat's tail) and hot plate response latencies (defined as the time that elapsed between the placement of a mouse or rat on a 55 degrees Celsius surface and a lick of the hind paw) were separately, but consecutively, measured before (baseline) and again at fixed intervals after subcutaneous or intracerebroventricular administration of one of the pentapeptide compounds of the invention, the Mosberg Pentapeptide, or after the administration of saline (controls). The cut-off latencies established to prevent tissue damage in the animals are 12 seconds or 14 seconds in the mouse and rat, respectively, in the Tail Flick Assay, and 40 seconds for both species in the Hot Plate Assay. The significance of any increase in tail flick response latency or hot plate response latency is determined using analyses of variance.

One way analyses of variance were used to determine the significance of the effect of the pentapeptides on response latencies. For these assays, the $ED_{50}$ value was defined as the dose of a pentapeptide compound which produced one half the maximum possible increase in latency (i.e., to 7.5 and 8.5 seconds in the mouse and rat, respectively, in the Tail Flick Assay, and to 25 seconds in both species in the Hot Plate Assay). Calculations of $ED_{50}$ values were based upon a least squared linear regression equation computed for the data at a time of peak effect, as described by D'Amour and Woolfe, supra.

"Activity" or "Inactivity" was determined at a particular concentration of the peptide by a significant increase in tail flick or hot plate latencies above normal latencies.

The data resulting from the Tail Flick Assay and the Hot Plate Assay are presented in Tables II and III below, respectively. The numbers in parentheses are calculated $ED_{50}$ values.

TABLE II

Data Generated from the Tail Flick Assay

| Peptide Tested | Subcutaneous | Intracerebro-ventricular | Example Number |
|---|---|---|---|
| Test Pentapeptide No. 1 (Mouse) | Active at 33 mpk | Active (0.28 μg) | Example 4 |
| Test Pentapeptide No. 1 (Rat) | Active at 30 mpk | Not Tested | Example 4 |
| Test Pentapeptide No. 2 (Mouse) | Active at 30 mpk | Active at 10 μg | Example 16 |
| Mosberg Pentapeptide (Mouse) | Not Tested | Active at 2.0 μg | None |

The data presented in Table II show that, when administered intracerebroventricularly, Test Pentapeptide No. 1 was ten times more active as an analgesic agent than the Mosberg Pentapeptide when tested in the same assay.

TABLE III

Data Generated from the Hot Plate Assay

| Peptide Tested | Subcutaneous | Intracerebro-ventricular | Example Number |
|---|---|---|---|
| Test Pentapeptide No. 1 (Mouse) | Not Tested | Active (0.20 μg) | Example 4 |
| Test Pentapeptide No. 2 (Mouse) | Active at 30 mpk | Active at 10 μg | Example 16 |
| Mosberg Pentapeptide (Mouse) | Not Tested | Active (1.4 μg) | None |

EXAMPLE 3

Opiate Binding Assay

Compounds within the present invention were also evaluated in an opioid radioligand binding assay, which measures the affinity of opioids for specific opioid receptors in rat forebrain, by their ability to displace the binding of radiolabeled ligands specifically bound to $\mu$ and/or $\delta$ opioid receptors isolated from rat brain. Compounds which are determined to be active in this in vitro assay will generally have opioid-like effects in animals, including analgesia, unless they are not bioavailable.

A purified homogenate of receptor membranes was prepared from the brains of the rats according to the method described by K. J. Chang et al., "Multiple Opiate Receptors: Enkephalins and Morphine Bind to Receptors of Different Specitivity," *J. Biol. Chem.*, 254, 2610–2618 (1979).

Male Charles River Sprague-Dawley albino rats weighing 150 to 300 g were stunned and decapitated. Their forebrains (minus the cerebellum and associated hindbrain) were quickly removed and rinsed in ice-cold 50 mM Tris buffer, pH 7.4, and homogenized in 20 volumes of buffer with a Polytron (Brinkman) at setting 6 for 30 seconds. The membranes were washed by centrifugation for 20 minutes at 30,000×g, followed by resuspension to twice the original volume. The homogenate was incubated at 25° for 1 hour, followed by centrifugation as above.

The resulting homogenate was then assayed for protein content according to the method described by Itzhaki et al., "A Micro-Biuret Method for Estimating Proteins," *Anal. Biochem.*, 9, 401–410 (1964). The final pellet was resuspended to a protein concentration of 10 mg protein per mL (assuming 6% of wet weight is protein) and 4 mL aliquots were rapidly frozen in liquid $N_2$.

The binding of compounds within the invention to the rat brain opiate receptor membrane preparation containing either $\delta$ or $\mu$ opioid receptors was measured using a modification of the method of C. B. Pert et al., "Properties of Opiate-Receptor Binding in Rat Brain," *Proc. Natl. Acad. Sci.*, 70, 2243–2247 (1972).

The opiate binding assays were conducted in triplicate at 37° C. in 50 mM TrisHCl buffer at pH 7.4 in a final volume of 1 mL, using varying concentrations of a compound of the invention. Each of three tubes contained 0.8 mL of homogenate containing approximately 1 mg/mL of protein. $^3$[H]-DAMPGO (2.0 nM) and $^3$[H]-DSLET (1.0 nM) were used to label the $\mu$ and $\delta$ opiate rat brain receptors, respectively.

The "percent displacement" of radiolabeled ligand ($^3$[H]-DAMPGO for the $\mu$ receptors and 3[H]-DSLET for the $\delta$ receptors) bound to the $\mu$ or $\delta$ opioid receptors by a compound of the present invention was determined at different concentrations of the compound (10 $\mu$M, 1 $\mu$M, 100 nM and/or 1 nM). Because the radiolabeled ligand and the compound compete with each other for the opiate receptor binding sites, the greater the per cent of displacement of the bound radiolabeled ligand, the better the compound is in terms of its ability to bind to the opiate receptors and, thus, the more potent the compound is. "Specific binding" of a compound of the present invention to the $\mu$ or the $\delta$ opiate rat brain receptors was defined as the difference between total binding and that in the presence of 10 $\mu$M of levorphanol.

For those compounds which bound particularly well to the opiate receptors, the mean $IC_{50}$ value (that concentration of a particular compound which is required to have 50 per cent of the bound radiolabeled ligand displaced from the opiate receptors) was calculated (nM). $IC_{50}$ values were determined from log-logit plots of concentration vs. time response curves. Comparison of $IC_{50}$ values in this assay system provides a measure of the receptor specificity of the tested compounds.

Finally, for those compound for which a mean $IC_{50}$ value was calculated for both the $\mu$ and $\delta$ opioid receptors, the ratio of the mean $IC_{50}$ values for the $\mu$ and $\delta$ opioid receptors was determined. This ratio indicates how specific a particular compound is for the $\delta$ opioid receptors. Thus, if the ratio of the mean $IC_{50}$ values is 1.0, the compound is approximately equally specific for both the $\mu$ and the $\delta$ opioid receptors. The greater the number is above 1.0, the more specific the compound is for the $\delta$ opioid receptors.

The results obtained from this opiate binding assay are shown in Table IV below, and correspond to the compound shown and described in the particular example identified below which corresponds thereto.

TABLE IV

Data Obtained from the Opiate Binding Assay

| Example Number | Per Cent Displacement | Mean $IC_{50}$ Value | Mean $IC_{50}$ $\mu/\delta$ Ratio |
|---|---|---|---|
| Example 4 ($\mu$) | — | 58.3 | 34 |
| Example 4 ($\delta$) | — | 1.7 | 34 |
| Example 20 ($\mu$) (Diastereomer A) | — | 24000 | 1000 |
| Example 20 ($\delta$) (Diastereomer A) | — | 24 | 1000 |
| Example 20 ($\mu$) (Diastereomer B) | 15% at 1 $\mu$M | NC | NC |
| Example 20 ($\delta$) (Diastereomer B) | 9% at 100 nM | NC | NC |
| Example 21 ($\mu$) (Diastereomer A) | 8% at 1 $\mu$M | NC | NC |
| Example 21 ($\delta$) (Diastereomer A) | 7% at 100 nM | NC | NC |
| Example 21 ($\mu$) (Diastereomer B) | 7% at 1 $\mu$M | NC | NC |
| Example 21 ($\delta$) (Diastereomer B) | — | 151 | NC |
| Example 16 ($\mu$) | — | 2.7 | 2 |
| Example 16 ($\delta$) | — | 1.7 | 2 |
| Example 41 ($\mu$) | — | 541.1 | 5 |
| Example 41 ($\delta$) | — | 106.8 | 5 |
| Example 15 ($\mu$) | — | 6.2 | 4 |
| Example 15 ($\delta$) | — | 1.4 | 4 |
| Example 22 ($\mu$) | — | 9.0 | 15 |
| Example 22 ($\delta$) | — | 0.6 | 15 |
| Example 23 ($\mu$) | — | 2.2 | 2 |
| Example 23 ($\delta$) | — | 0.9 | 2 |
| Example 24 ($\mu$) | — | 10.8 | 1.6 |
| Example 24 ($\delta$) | — | 6.8 | 1.6 |

— = Not Applicable (Because the Mean $IC_{50}$ Value was Calculated)
NC = Not Calculated

EXAMPLE 4

2,6-dimethyl-L-tyrosyl-3-mercapto-D-valylglycyl-L-phenylalanyl-3-mercapto-D-valine, cyclic (2→5)-disulfide

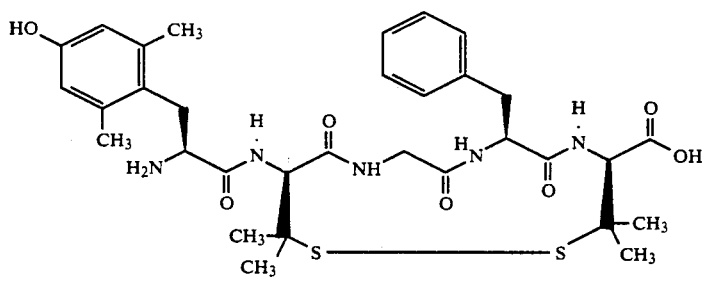

L,D,L,D $N^\alpha$-Boc-(S-p-methylbenzyl)D-penicillamine was attached to the solid phase resin support via an ester linkage using a modification of the procedure of Gisin (*Helv. Chim. Acta*, 56, 1476 (1973)).

Briefly, $N^\alpha$-Boc-(S-p-methylbenzyl)D-penicillamine (7.96 g, 22.5 mmol) was dissolved in 160 mL of dry, $N_2$-purged dimethylforamide (DMF). To this solution was added 20 g of Merrifield resin (chloromethylated polystyrene cross linked with 1% divinylbenzene; 1.34 meq Cl/gram, Lab Systems) and 5.15 g (26.5 mmol) of $CsHCO_3$, and the suspension was stirred at 50° C. under anhydrous conditions for 72 hours. Progress of the reaction was followed by disappearance of $N^\alpha$-Boc-(S-p-methylbenzyl)D-penicillamine, which was assessed by analytical high power liquid chromatography (HPLC). The HPLC indicated a greater than 99% completion at 72 hours.

The product, $N^\alpha$-Boc-(S-p-methylbenzyl)D-penicillamine-Merrifield resin, was filtered, washed with 3×75 mL of DMF, 3×75 mL of DMF/$H_2O$ (9:1), 3×75 mL of DMF, and 3×75 mL of ethanol (ETOH) and dried under vacuum.

1.06 g of $N^\alpha$-Boc-(S-p-methylbenzyl)D-penicillamine-Merrifield resin was placed in the reaction vessel of a Vega Biotechnologies 250C automated solid phase peptide synthesizer, and $N^\alpha$-Boc-2,6-dimethyl-L-tyrosyl-S-p-methylbenzyl-D-penicillaminyl-glycinyl-L-phenylalaninyl-S-p-methylbenzyl-D -penicillaminyl-resin was prepared by stepwise addition of the protected amino acids, $N^\alpha$-Boc-L-phenylalanine, $N^\alpha$-Boc-glycine, $N^\alpha$-Boc-S-p-methylbenzyl-D-penicillamine, and $N^\alpha$-Boc-2,6-dimethyl-L-tyrosine using Coupling Agenda 1:

Coupling Agenda 1

1. Wash the peptide resin with methylene chloride ($CH_2Cl_2$) for 2 minutes, and then repeat this 3 additional times;
2. Treat the peptide resin with a solution of trifluoroacetic acid (TFA):anisole:$CH_2Cl_2$ (48:2:50) for two minutes;
3. Treat the peptide resin with a solution of TFA:anisole:$CH_2Cl_2$ (48:2:50) for 20 minutes;
4. Wash the peptide resin with $CH_2Cl_2$ for 2 minutes, and repeat this 3 additional times;
5. Treat the peptide resin with a solution of diisopropylethylamine (DIEA):$CH_2Cl_2$ (10:90) for 3 minutes, and repeat this 1 additional time;
6. Wash the peptide resin with $CH_2Cl_2$ for 2 minutes, and repeat this 3 additional times;
7. Test a small portion of the resin with the ninhydrin test of Kaiser et al., *Anal. Bioch.*, 34, 595 (1970). If the test is positive, proceed to step 8, but if it is negative, repeat steps 3-7;
8. Add 3 equivalents of appropriate $N^\alpha$-Boc-amino acid dissolved in $CH_2Cl_2$ or DMF, 2.4 equivalents of dicyclohexylcarbodiimide (DCC) dissolved in $CH_2Cl_2$, and 2.4 equivalents of 1-hydroxybenzotriazole (HOBT) dissolved in DMF. Allow the reaction to proceed with gentle agitation for 2 hours;
9. Wash the peptide resin with $CH_2Cl_2$ for 2 minutes, and repeat this 2 additional times;
10. Wash the peptide resin with EtOH for 2 minutes, and repeat this 2 additional times;
11. Wash the peptide resin with $CH_2Cl_2$ for 23 minutes, and repeat this 3 additional times; and
12. Test a small portion of the resin with the ninhydrin test of Kaiser et al., supra. If the test is positive, repeat steps 8-12. If test is negative, repeat steps 1-12 for the next $N^\alpha$-Boc amino acid being added to the peptide being synthesized.

The $N^\alpha$-Boc-2,6-dimethyl-L-tyrosyl-S-p-methylbenzyl-D-penicillaminyl-glycinyl-L-phenylalaninyl-S-p-methylbenzyl-D -penicillaminyl-resin was transferred to a sintered glass funnel and dried in vacuo to yield 1.35 g.

1.3 g of this compound was then treated with 0.65 g of p-thiocresol, 0.65 g of cresol, and 20 mL of anhydrous hydrofluoric acid (HF) at 0° C. for 45 minutes to effect the cleavage of the peptide from the resin, and the removal of the N-terminal Boc, as well as the deprotection of the D-penicillamine sulfurs.

Following evaporation of excess hydrofluoric acid, the resin was extracted with 100 mL of diethylether ($Et_2O$), the filtrate being discarded, followed by extraction with 20 mL of a mixture of DMF and 80% acetic acid (90/10).

This latter extract was diluted with 200 mL of a solution of 0.1% TFA in $H_2O$, and was purified on a Vydac 218TP ™ reverse phase HPLC column (2.2 cm×25 cm) using a linear gradient of 10-50% solvent B (0.1% TFA in $CH_3CN$) in solvent A (0.1% TFA in $H_2O$).

The linear disulfhydryl-containing pentapeptide eluting in about 65 mL at 33% solvent B, was collected, diluted with 200 mL of $H_2O$, and the pH of the solution was adjusted to 8.5 with $NH_4OH$. 60 mL of 0.01 M $K_3Fe(CN)_6$ in water was added to the solution, and the reaction was allowed to proceed with stirring for 2 hours. An additional 30 mL of 0.01 M $K_3Fe(CN)_6$ solution was added, and the reaction was allowed to continue for an additional 1 hour. Analytical HPLC showed that the oxidation reaction to the cyclic disulfide-containing pentapeptide was essentially complete. The mixture was acidified to pH 4, stirred for 20 minutes with 10 mL (settled volume) of anion exchange resin (AG 3×4 A, Cl form), and filtered. The filter was washed with 20 mL of a mixture of DMF and 80% acetic acid (90:10), and the wash was added to the filtrate.

The resulting solution was purified by HPLC on a Vydac 218TP ™ reversed phase HPLC column (2.2 cm×25 cm) using a linear gradient of 10–50% solvent B in Solvent A, and lyophilized. This procedure yielded 54 mg of the title product, which was determined to be greater than 99% pure by analytical HPLC, and which was found to have the appropriate molecular weight of 673 by analysis via fast atom bombardment (FAB) mass spectrometry.

EXAMPLE 5

2,6-dimethyl-L-tyrosyl-3-mercapto-D-valylglycyl-L-phenylalanyl-3-mercapto-L-valine, cyclic (2→5)-disulfide

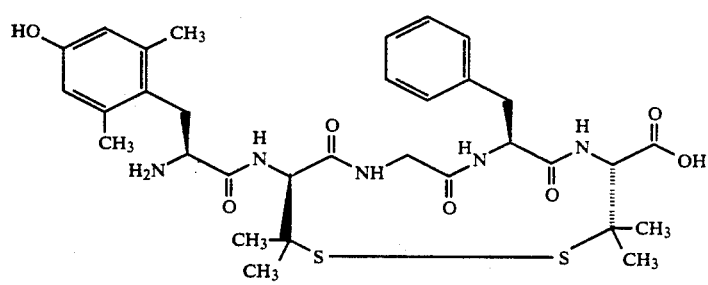

L,D,L,L

The title product was synthesized from N<sup>α</sup>-Boc-(S-p-methylbenzyl)L-penicillamine by the method of Example 4. This compound was found to be greater than 99% pure by analytical HPLC, and to have the appropriate molecular weight of 673 by analysis via FAB mass spectrometry.

EXAMPLE 6

2,6-dimethyl-L-tyrosyl-3-mercapto-D-valylglycyl-4-fluoro-L-phenylalanyl-3-mercapto-D-valine, cyclic (2→5)-disulfide

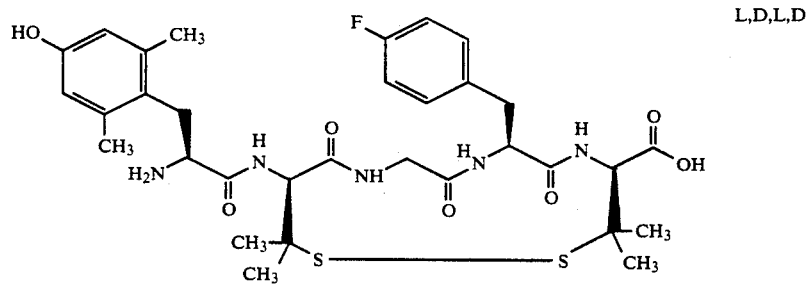

L,D,L,D

The title compound was prepared by the method of Example 4 wherein Boc-L-(p-fluoro)phenylalanine replaced Boc-L-phenylalanine in the synthetic sequence. This pentapeptide was determined to be greater than 99% pure by analytical HPLC, and to have the appropriate molecular weight of 691 by analysis via FAB mass spectrometry.

EXAMPLE 7

2,6-dimethyl-L-tyrosyl-3-mercapto-D-valylglycyl-4-chloro-L-phenylalanyl-3-mercapto-D-valine, cyclic (2→5)-disulfide

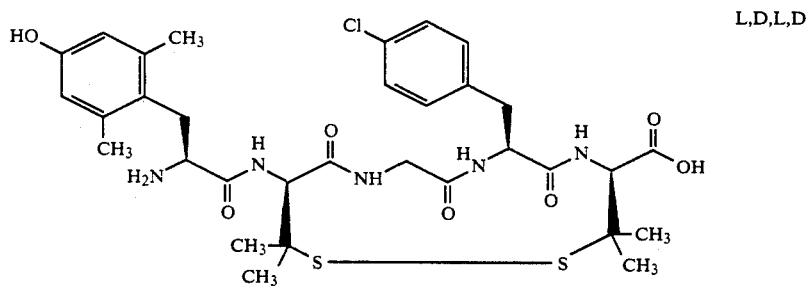

L,D,L,D

The title compound is synthesized by the method of Example 4 wherein Boc-(p-chloro)-L-phenylalanine replaces Boc-L-phenylalanine in the synthetic sequence.

EXAMPLE 8

2,6-dimethyl-L-tyrosyl-D-cysteinylolycyl-4-chloro-L-phenylalanyl-3-mercapto-D-valine, cyclic (2→5)-disulfide

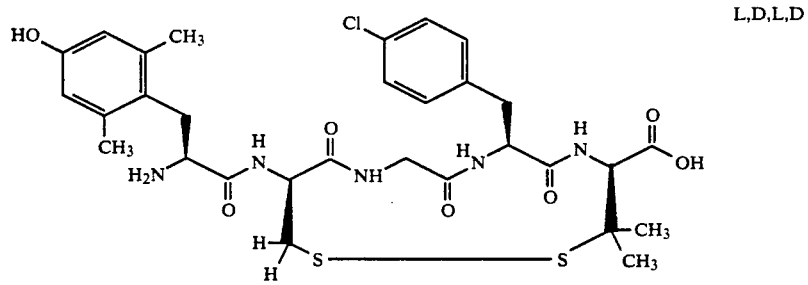

The title compound is prepared by the method of Example 4 wherein Boc-(S-p-methylbenzyl)-D-cysteine and Boc-(p-chloro)-L-phenylalanine replace Boc-(S-p-methylbenzyl)D-penicillamine2 and Boc-L-phenylalanine, respectively, in the synthetic sequence.

EXAMPLE 9

2,6-dimethyl-L-tyrosyl-3-mercapto-D-valylglycyl-4-chloro-D-phenylalanyl-3-mercapto-D-valine, cyclic (2→5)-disulfide

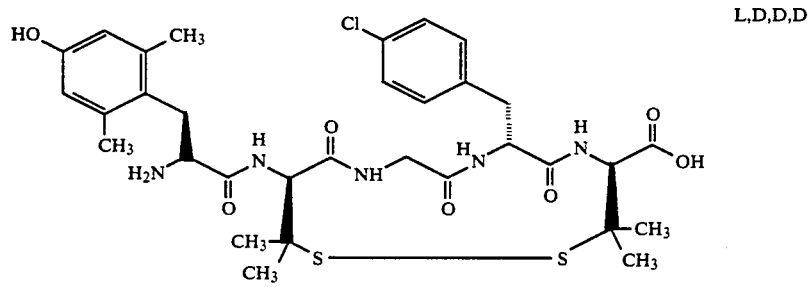

The title compound is generated by the method of Example 4 wherein Boc-(p-chloro)-D-phenylalanine replaces Boc-L-phenylalanine in the synthetic sequence.

EXAMPLE 10

2-methyl-L-tyrosyl-3-mercapto-D-valylglycyl-L-phenylalanyl-3-mercapto-D-valine, cyclic (2→5)-disulfide

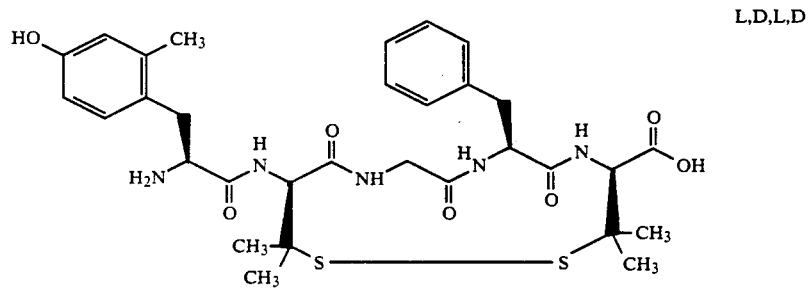

The title compound is synthesized by the method of Example 4 wherein Boc-2,6-dimethyl-L-tyrosine is replaced by Boc-2-methyl-L-tyrosine in the synthetic sequence.

EXAMPLE 11

O,2,6-trimethyl-L-tyrosyl-3-mercapto-D-valylglycyl-L-phenylalanyl-3-mercapto-D-valine, cyclic (2–5)-disulfide

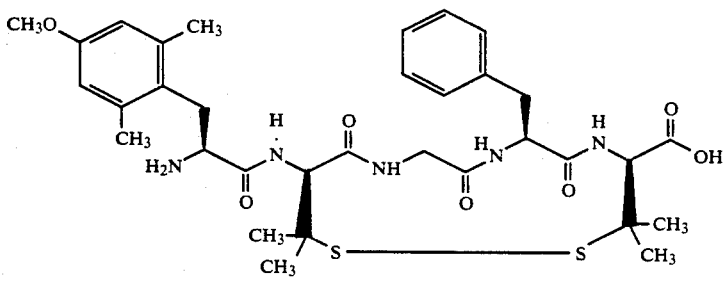

L,D,L,D

The title compound is prepared by the method of Example 4 wherein Boc-2,6-dimethyl-L-tyrosine is replaced by Boc-2,6,O-Trimethyl-L-tyrosine in the synthetic sequence.

The L-isomer is synthesized by the process described for the DL-isomer in U.S. Pat. No. 4,760,180.

Briefly, Boc-2,6-dimethyltyrosine (3.0 g, 9.70 mmol) was stirred with methyl iodide (6.88 g, 48.5 mmol) and potassium carbonate (5.36 g, 38.8 mmol) in dimethylformamide (DMF) (50 mL) for 17 hours in a 100 mL round-bottom single necked flask, protected from moisture with a drying tube. The reaction mixture was partitioned between water and diethyl ether. The aqueous phase was washed twice with ether and the organic fractions were combined, dried (MgSO4), filtered, and stripped to a white solid. Used as is NMR: methoxy singlets at ʃ 3.51 and 3.66.

0-Methyl-Boc-2,6-dimethyltyrosine methyl ester (directly from the above reaction, 9.7 mmol if yield was quantitative) was dissolved in methanol (70 mL) and cooled in an ice bath. A solution of NaOH (3.1 g, 77.6 mmol) in water (20 mL) was added. The mixture was stirred for three hours. A TLC in 1:1 Skelly B: Ethyl acetate (EtoAc) on silica slides showed that the reaction was complete. A solution of KHSO4 (10.6 g, 77.6 mmol) in water (75 mL) was added. The mixture was stripped to a lower volume to remove methanol, and extracted twice with CH2Cl2 (methylene chloride). The organic fractions were combined, dried (MgSO4), filtered, and stripped. The weight was 2.6 g. NMR: one methoxy singlet only, at ʃ 3.66.

EXAMPLE 12

O-acetyl-2,6-dimethyl-L-tyrosyl-3-mercapto-D-valylglycyl-L-phenylalanyl-3-mercapto-D-valine, cyclic (2→5)-disulfide

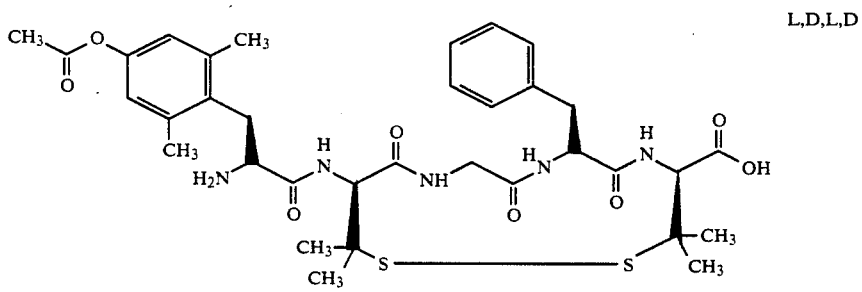

L,D,L,D

The product of Example 4 is converted to its Boc derivative by treatment with di-t-butyldicarbonate (1.1 eq) and sodium hydroxide (1.2 eq) in t-butanol/H2O (1:2 in 2 mL/mmol of product of Example 4) at room temperature. This material is then reacted with acetic anhydride. Aqueous work up of this reaction yields the Boc-protected title product. Exposure of this derivative to 6N hydrochloric acid (HCl) in dioxane at room temperature under an argon atmosphere provides the title compound.

EXAMPLE 13

2,6-dimethyl-L-tyrosyl-β-mercapto-D-α-aminobutyrylglycyl-L-phenylalanyl-3-mercapto-D-valine, cyclic (2→5)-disulfide

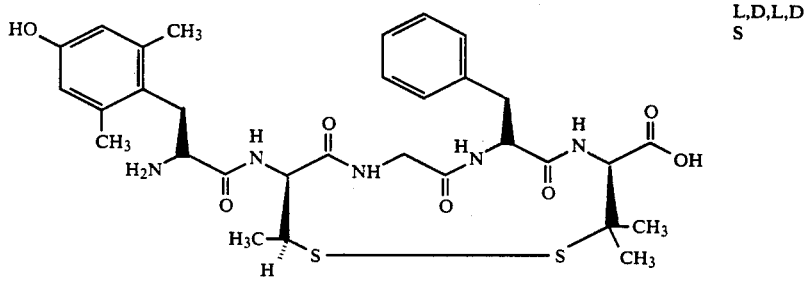

L,D,L,D
S

-continued

L,D,L,D
R

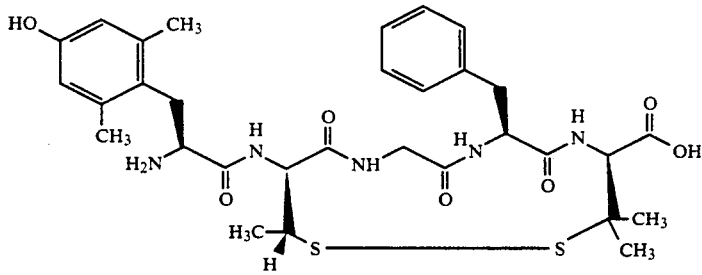

The title peptides are obtained by the method of Example 4 wherein Boc-(S-p-methylbenzyl)-β-methyl-D-cysteine replaces Boc-(S-p-methylbenzyl)D-penicillamine² in the synthetic sequence.

EXAMPLE 14

2,6-dimethyl-L-tyrosyl-3-mercapto-D-valylglycyl-L-phenylalanyl-L-cysteine, cyclic (2→5)-disulfide was utilized. A double coupling procedure was also used to load Boc-D-Pen(S-p-methylbenzyl) onto the resin. The peptides were removed from the resin and deprotected with anhydrous hydrogen fluoride (HF, 10 mL/g of resin-bound peptide) containing anisole (1 mL/g of resin-bound peptide) at 0° C. for 1 hour on an HF-Reaction Apparatus. After evaporation of the hydrogen fluoride, the residue was triturated successively

L,D,L,D

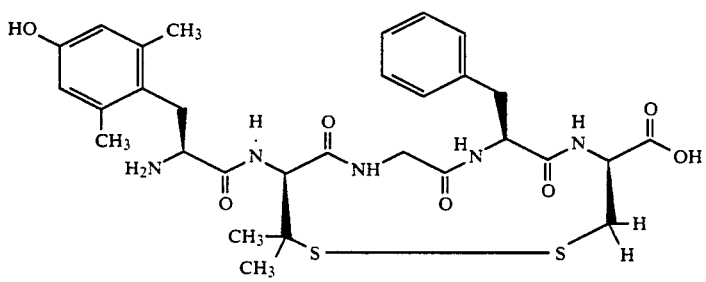

The title product is synthesized by the method of Example 4 wherein Boc-(S-p-methylbenzyl)-D-cysteine replaces Boc-(S-p-methylbenzyl)D-penicillamine⁵ in the synthetic sequence.

EXAMPLE 15

2,6-dimethyl-L-tyrosyl-3-mercapto-D-valylglycyl-L-phenylalanyl-3-mercapto-D-valinamide, cyclic (2→5)-disulfide with ether. The peptide was extracted with 50 mL of 80% acetic acid (HOAc), and this solution was lyophilized. The material was then oxidized with K₄Fe(CN)₆ and purified by HPLC, as described in Example 4, to produce the title compound (95 mg).

$[\alpha]_D = -82.7°$ (MeOH).

Analysis Calculated for $C_{32}H_{44}N_6O_6S_2$+HF+HOAc+H₂O (MW=770.94): C, 52.97; H, 6.67; N, 10.90; S, 8.32. Found: C, 52.31; H 6.36; N, 11.15; S, 8.33.

L,D,L,D

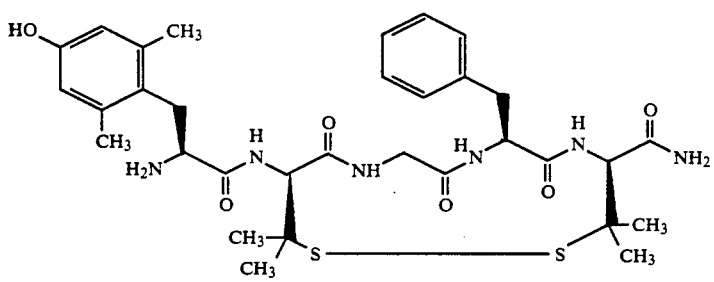

The title compound was synthesized on an Applied Biosystems Inc. (ABI) Model 430A peptide synthesizer using p-methyl-benzhydrylamine hydrochloride resin (~0.5 mequiv/g). For the amino acids Boc-2,6-dimethyl-L-tyrosine (Boc-DMT) and Boc-D-Pen(S-p-methylbenzyl), a regular double coupling program procedure

EXAMPLE 16

-dimethyl-L-tyrosyl-3-mercapto-D-valylglycyl-L-phenylalanyl-3-mercapto-D-valine, cyclic (2→5)-disulfide, methyl ester

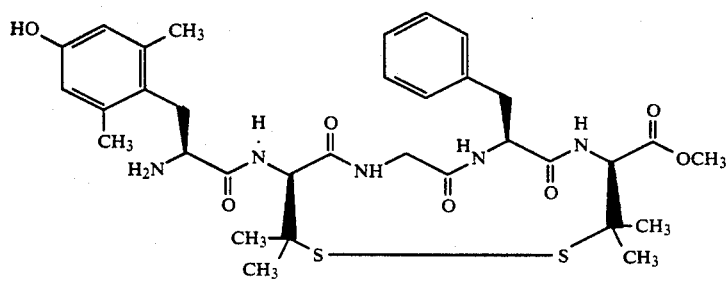

L,D,L,D

The title material was obtained using N-[(1,1-dimethylethoxy)carbonyl]-2,6-dimethyl-L-tyrosyl-3-mercapto-D -valylglycyl-L-phenylalanyl-3-mercapto-D-valine, cyclic (2→5)-disulfide, methyl ester, prepared as described below in Example 31 (7.4 g, 9.4 mmol) using the method described below in Example 30. A 6.8 g (100%) sample of the title compound was obtained as a white solid Analysis calculated for $C_{33}H_{45}N_5O_7S_2 + HCl + H_2O (MW = 742.36)$: C, 53.39; H, 6.52; N, 9.43; S, 8.64; Cl, 4.78. Found: C, 53.04;H, 6.34; N, 9.13 ; S, 8.65; Cl, 4.50

EXAMPLE 17

2,6-dimethyl-L-tyrosyl-3-mercapto-D-valylglycyl-phenylalanyl-N-ethyl-3-mercapto-D-valinamide, cyclic (2→5)-disulfide

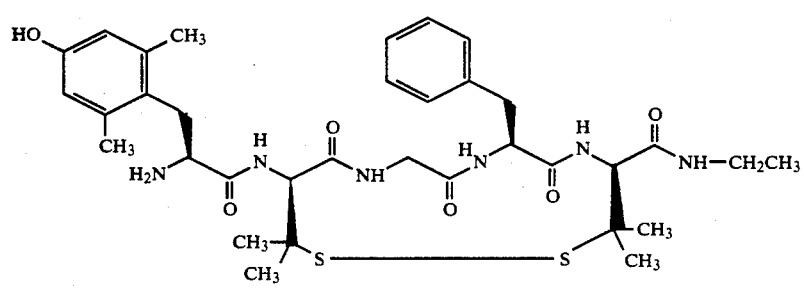

L,D,L,D

The title product is synthesized by the method of Example 4 wherein the Merrifield resin is treated with excess ethyl amine before $N^\alpha$-Boc-(S-p-methylbenzyl)D-penicillamine is attached to the solid phase resin support via the amide linkage, as described in *Internat. Peptide Protein Res.*, 25, 414–420, 1985. The title peptide is isolated after HF cleavage from the resin, cyclization, and chromatographic purification.

EXAMPLE 18

2,6-dimethyl-O-[(2-methylpropoxy)carbonyl]-L-tyrosyl-3-mercapto-D-valylglycyl-L-phenylalanyl-3-mercapto-D -valine, cyclic (2→5)-disulfide

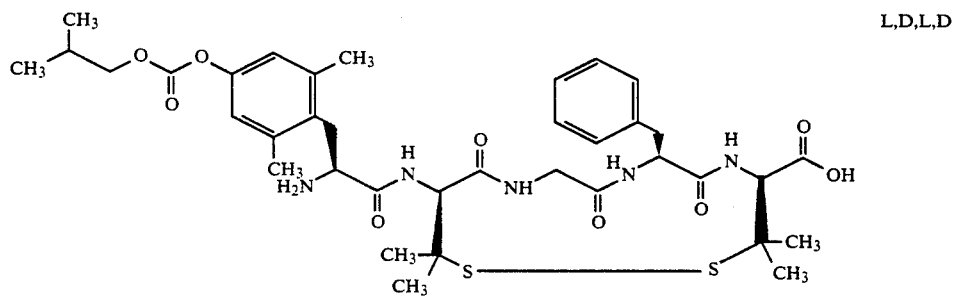

L,D,L,D

The product of Example 4 is converted to its Boc derivative in the manner described in Example 12. This material is then treated with isobutylchloroformate (2 eq) in $CH_2Cl_2$. Aqueous work up of this reaction yields the Boc-protected title product. Exposure of this derivative to 6N HCl in dioxane at room temperature under an argon atmosphere provides the title cyclic peptide.

EXAMPLE 19

O-[(ethylamino)carbonyl-2,6-dimethyl-L-tyrosyl-mercapto-D-valylglycyl-L-phenylalanyl-D-cysteine, cyclic (2→5)-disulfide

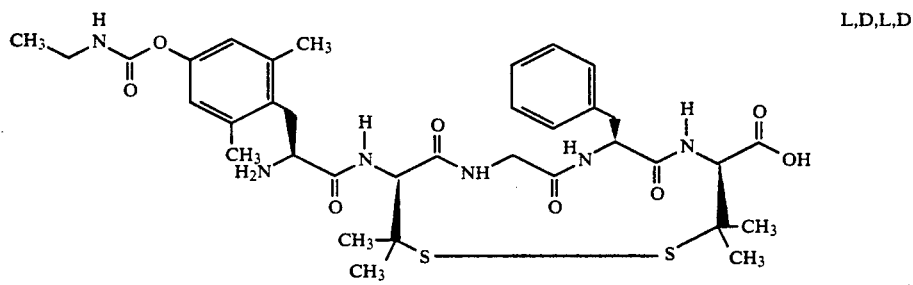

L,D,L,D

The Boc derivative of the product of Example 4 is synthesized in the manner described in Example 12. This material is then treated with ethylisocyanate (2 eq), and N-methylmorpholine (2 eq) in $CH_2Cl_2$. Aqueous work up of this reaction yields the Boc-protected title product. Exposure of this derivative to 6N HCl in dioxane at room temperature under an argon atmosphere yields the title cyclic peptide.

EXAMPLE 20

2,3,6-trimethyl-L-tyrosyl-3-mercapto-D-valylglycyl-L-phenylalanyl-3-mercapto-D-valine, cyclic (2→5) disulfide The title peptides were synthesized by the method of Example 4 wherein Boc-2,3,6-trimethyl-DL-tyrosine replaced Boc-2,6-dimethyl-L-tyrosine in the synthetic sequence. This procedure yielded the two diastereomers which were, as described in Example 4, separated by HPLC and found to have the appropriate molecular weight of 688 by fast atom bombardment mass spectrometric analysis. Diastereomer A (7.0 mg) had an HPLC retention time of 34.3 minutes on a 0.46 cm×25 cm, Vydac 218TpS4, C-18 reverse phase column, eluting with a gradient of 0% to 70% solvent B (01.% TFA in acetonitrile) in solvent A (0.1% TFA in water). Under identical conditions, diastereomer B (10.8 mg) had a retention time of 33.5 minutes. The stereochemical identity of each diastereomer is unknown.

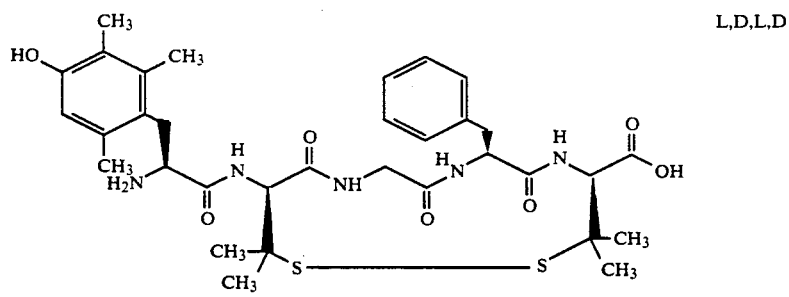

L,D,L,D

Diastereomers A and B

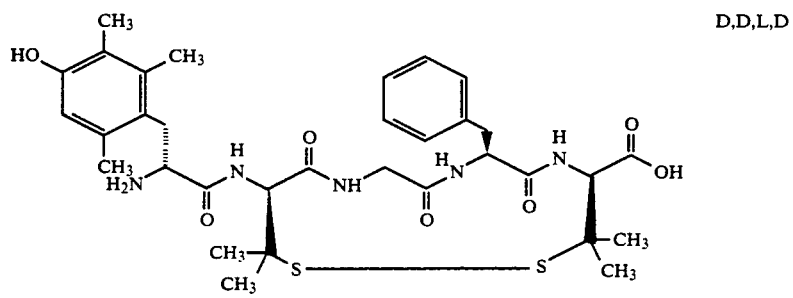

D,D,L,D

EXAMPLE 21

3-hydroxy-2,4-dimethyl-L-phenylalanyl-3-mercapto-D-valyglycyl-L-phenylalanyl-3-mercapto-D-valine, cyclic (2→5)-disulfide

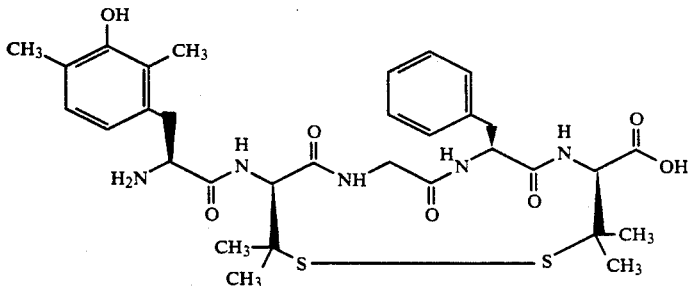

Diastereomers A and B

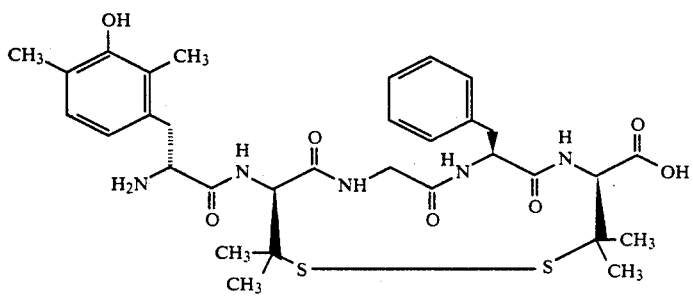

The title peptides were synthesized by the method of Example 4 wherein Boc-3-hydroxy-2,4-dimethyl-DL-phenylalanine replaced Boc-2,6-dimethyl-L-tyrosine in the synthetic sequence. This procedure yielded the two diastereomers which were separated by HPLC, as described in Example 4, and found to have the appropriate molecular weight of 674 by fast atom bombardment mass spectrometric analysis. Diastereomer A (4.1 mg) had an HPLC retention of 32.8 minutes on a 0.46 cm×25 cm, Vydac 218TPS4, C-18 reverse phase column eluting with a gradient of 0% to 70% solvent B in solvent A, as described above in Example 20. Under identical conditions, diastereomer B (7.3 mg) had a retention time of 35.4 minutes. The stereochemical identity of each diastereomer is unknown.

EXAMPLE 22

2,6-dimethyl-L-tyrosyl-3-mercapto-D-valylglycyl-4-chloro-L-phenylalanyl-3-mercapto-D-valinamide, cyclic (2→5)-disulfide

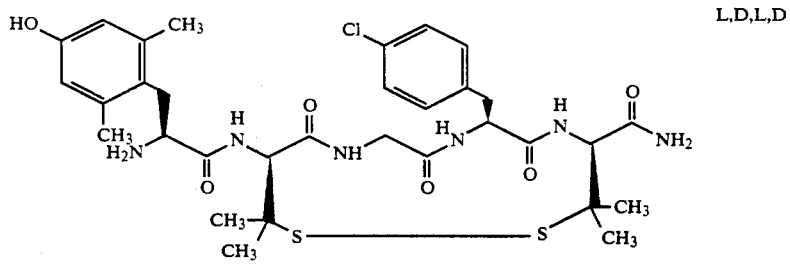

The title peptide was synthesized by the method of Example 15 wherein the phenylalanine in the fourth position (Phe[4]) is replaced with p-chloro-phenylalanine. A mg sample of the title compound was obtained.

Analysis Calculated for $C_{32}H_{43}N_6O_6S_2Cl + 2.0$ trifluoro acetic acid (TFA)+$H_2O$ (MW=953.38): C, 45.35; H, 4.97; N, 8.81; S, 6.73. Found: C, 45.47; H, 5.19; N, 8.92; S,

EXAMPLE 23

2,6-dimethyl-L-tyrosyl-3-mercapto-D-valylglycyl-4-fluoro-L-phenylalanyl-3-mercapto-D-valinamide, cyclic (2→5)-disulfide

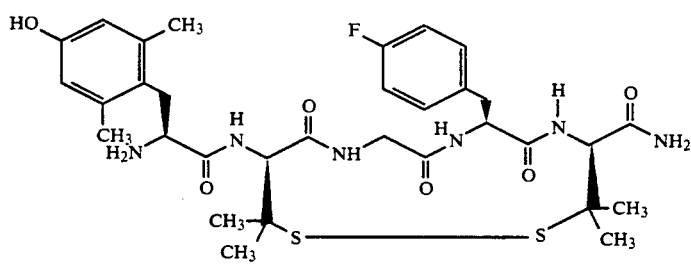

The title peptide was synthesized by the method of 5 wherein the phenylalanine in the fourth position (Phe⁴) is replaced with p-fluoro-phenylalanine. A 30 mg sample of the title compound was obtained.

Analysis Calculated for $C_{32}H_{43}N_6O_6S_2F+2.5$ TFA+2.5 $H_2O$ (MW=1020.96): C, 43.53; H, 4.99; N, 8.23; S, 6.28. Found: C, 43.01; H, 4.92; N, 8.71; S, 6.27.

EXAMPLE 24

2,6-dimethyl-L-tyrosyl-3-mercapto-D-valylglycyl-3-cyclohexyl-L-alanyl-3-mercapto-D-valinamide, cyclic (2→5)-disulfide

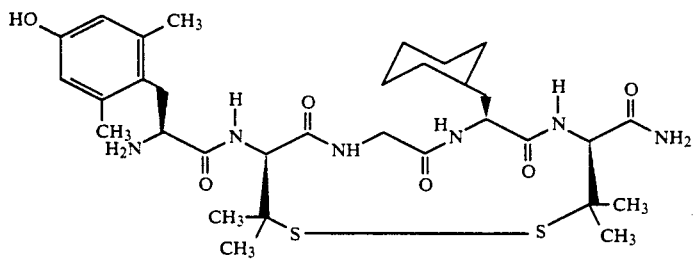

The title peptide was synthesized by the method of Example 15 wherein the phenylalanine in the fourth position (Phe⁴) is replaced with hexahydrophenylalanine. A 30 mg sample of the title compound was obtained. Analysis Calculated for $C_{32}H_{49}N_6O_6S_2+2.0$ TFA (MW=905.96): C, 47.73; H, 5.67; N, 9.28; S, 7.08. Found: C, 47.43; H, 6.15; N, 6.46; S, 7.23.

EXAMPLE 25

2,6-dimethyl-L-tyrosyl-3-mercapto-D-valylglycyl-L-alanyl-3-mercapto-D-valinamide, cyclic (2→5)-disulfide

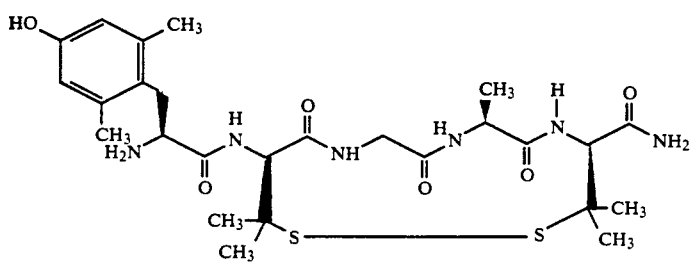

The title peptide is synthesized by the method of Example 15 wherein the phenylalanine in the fourth position (Phe⁴) is replaced with alanine.

EXAMPLE 26

N-N-[N-(1,1-dimethylethoxy)carbonyl-3-(triphenylmethyl)thio]-D-valyl]glycyl]-L-phenylalanine, methyl ester

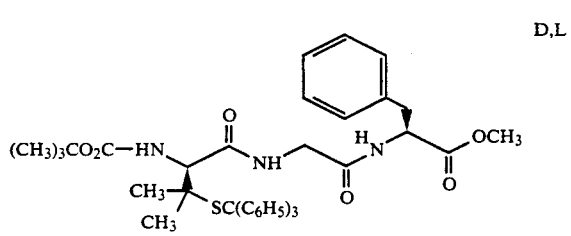

A tetrahydrofuran (THF) (400 mL) solution of $N^\alpha$-Boc-S-trityl-D-penicillamine (26.5 g, 0.054 mol) was cooled under an argon atmosphere to −20° C. N-methylmorpholine (NMM) (5.92 mL, 0.054 mol) was added, followed immediately by isobutylchloroformate (IBCF) (7 mL, 0.054 mol). Thirty minutes later, a solution of glycine phenylalanine methylester hydrochloride (14.7 g, 0.054 mol) and NMM (5.92 mL, 0.054 mol) in DMF (80 mL) was added to the reaction. The reaction was allowed to warm to room temperature overnight. After removing most of the solvent in vacuo, ethylacetate (EtOAc) (250 mL) was added to the reaction and the solution was washed with 1×0.5 N KHSO₄ (200 mL). The aqueous layer was back extracted with an additional 240 mL of EtOAc. The combined organic layers were washed with 1×300 mL 0.5 N KHSO₄, 2×250 mL saturated NaHCO₃, and 2×250 mL brine. After drying the solution over anhydrous Na₂SO₄, all solvent was removed under reduced pressure and the title product (38 g, 99%) was obtained as a white solid.

Analysis Calculated for C₄₁H₄₇N₃O₆S+1.7 H₂O (MW=740.54): C, 66.50; H, 6.87; N, 5.07; S, 4.33. Found: C, 66.24; H, 6.67; N, 5.41; S, 4.08.

EXAMPLE 27

N-[N-[N-[(1,1-dimethylethoxy)carbonyl-3-(triphenylmethyl)thio]-D-valylglycyl]-L-phenylalanine

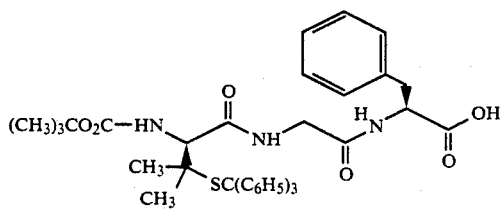

D,L

The product of Example 26 (33.5 g, 0.047 mol), dissolved in THF (200 mL) was combined with 0.5 M LiOH (0.071 mol, 141 mL). After stirring this mixture at room temperature under argon for 30 minutes, all solvent was removed in vacuo. The residue was acidified with 0.5 N KHSO₄ and extracted into EtOAc. The organic layer was then washed with water and brine, dried over Na₂SO₄, and stripped of all solvent in vacuo to produce the crude product as a yellow foam. The title material was purified by flash chromatography using EtOAc/n-hexane/HOAc (60/40/0.5) increasing to EtOAc/HOAc (99.5/0.5) as eluant. A 24.1 g sample (73%) of the title product was isolated.

Analysis Calculated for C₄₀H₄₅N₃O₆S+2.0 H₂O (MW=731.92): C, 65.64; H, 5.75; N, 5.74; S, 4.38. Found: C, 65.83; H, 6.50; N, 6.14; S, 3.65.

EXAMPLE 28

N-[N-[N-[N-(1,1-dimethylethoxy)carbonyl]-3-[(triphenylmethyl)thio]-D-valylglycyl-L-phenylalanyl]-3-mercapto-D-valine, methyl ester

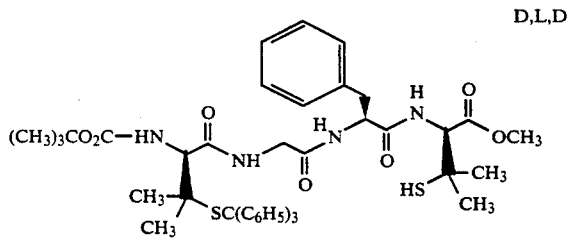

D,L,D

To a THF (200 mL) solution of the title compound of Example 27 (22.0 g, 0.0316 mol) under argon and cooled to −78° C., were added 3.49 mL (0.0316 mol) of NMM and immediately thereafter, 4.21 mL (0.0324 mol) of IBCF. The reaction was allowed to warm to 0° C. and, after 30 minutes at this temperature, was cooled to −78° C. A solution of D-penicillamine methylester hydrochloride (6.35 g, 0.0316 mol) and NMM (3.49 mL, 0.0316 mol) in DMF (40 mL) was added to the reaction. The reaction was allowed to warm to room temperature and stirred overnight. After removing most of the solvent in vacuo. EtOAc (700 mL) was added to the reaction, and the solution was washed with I x 0.5 N KHSO₄ (200 mL). The aqueous layer was back extracted with an additional 200 mL of EtOAc. The combined organic layers were then washed with 1×300 mL 0.5 N KHSO₄, 2×250 mL d NaHCO₃, and 2×250 mL brine. The solution was dried (Na₂SO₄) and all solvent removed under reduced pressure to yield 25.5 g (96%) of the crude desired title material, which was used in Example 29 without further purification.

EXAMPLE 29

N-[(1,1-dimethylethoxy)carbonyl]-3-mercapto-D-valylglycyl-L-phenylalanyl-3-mercapto-D-valine, cyclic (2→5)-disulfide methyl ester

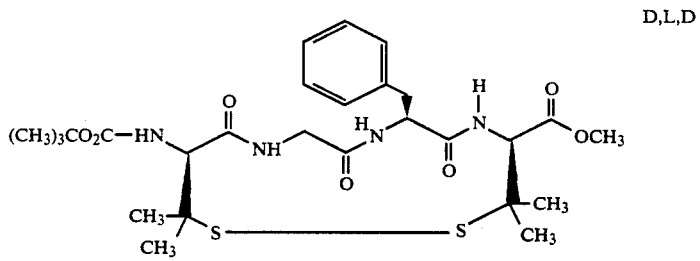

D,L,D

Glacial acetic acid (HOAc, 2175 mL) and iodine (3.4 g, 0.0134 mol) were combined in a 12-L flask equipped with a mechanical stirrer, nitrogen inlet and a 1-L dropping funnel. After the iodine had dissolved, water (660 mL) was added, and the solution was stirred for 15 minutes.

The product of Example 28 (9.21 g, 0.01095 mmol) was dissolved in HOAc (2175 mL) and diluted with water (660 mL). This solution was added dropwise to the reaction flask over a period of 2 hours. After stirring an additional 20 minutes, the excess iodine was reduced by titration with 1 N Na₂SO₃ (30 mL) to yield a colorless solution. Sodium hydroxide (1 N, 21.9 mL) was added to the reaction, and all solvent was removed in vacuo. The residue was dissolved in EtOAc (250 mL) and washed successively with 200 mL portions of 0.25 N Na₂SO₃, water and brine. The solution was dried (Na₂SO₄) and all solvent was removed in vacuo. The residue was triturated in Et₂O at −4° C. for 16 hours. After filtering, the solid was washed three times with Et₂O and air dried to give 3.53 g (54%) of the title material.

Analysis Calculated for $C_{27}H_{40}N_4O_7S_2 + 2.8\ H_2O$ (MW=647.21): C, 50.11; H, 7.10; N, 8.66; S, 9.91. Found: C, 50.35; H, 6.36; N, 8.56; S, 9.50.

EXAMPLE 30

3-mercapto-D-valylglycyl-L-phenylalanyl-3-mercapto-D-valine, cyclic (2→5)-disulfide, methyl ester, monohydrochloride

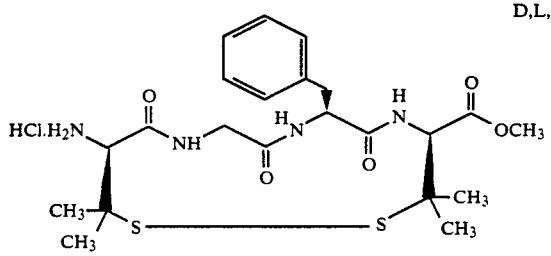

To the title product synthesized in Example 29 (6.5 g, 10.9 mmol) dissolved in methylene chloride (CH₂Cl₂, 158 mL) and under an argon atmosphere, was added 6.9 N HCl/dioxane (15.8 mL, 0.11 mol). The reaction was allowed to stir for 60 minutes before the reaction was filtered, and all solvent was removed in vacuo. The solid residue was triturated in Et₂O and dried in vacuo to give 5 g (86%) of the fairly-pure title material. This compound was used without further purification in the manner described in Example 31, below.

$[\alpha]_D = -70.4°$ (MeOH)

EXAMPLE 31

N-[(1,1-dimethylethoxy)carbonyl]-2,6-dimethyl-L-tyrosyl-3-mercapto-D-valylglycyl-L-phenylalanyl-3-mercapto-D-valine, cyclic (2→5)-disulfide, methyl ester

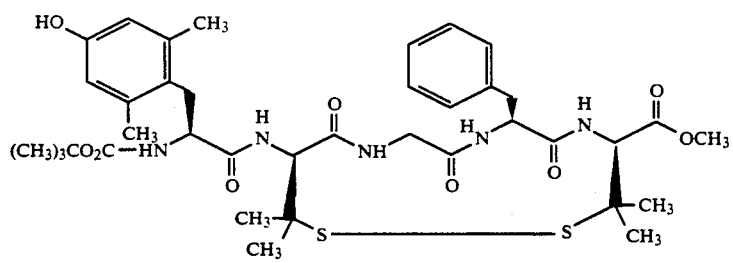

$N^\alpha$-Boc-2,6-dimethyl-L-tyrosine (2.9 g, 9.4 mmol) was coupled to the product of Example 30 (5.0 g, 9.4 mmol) by the method described above in Example 28. A 3.1 g (42%) sample of the desired title material was isolated as a white solid.

$[\alpha]_D = +9.8°$ (CHCl₃) Analysis Calculated for $C_{38}H_{53}N_5O_9S_2 + 0.5\ H_2O$ (MW=797.00): C, 57.27; H, 6.83; N, 8.79; S, 8.05. Found: C, 56.97; H, 6.82; N, 8.63; S, 8.04.

EXAMPLE 32

N-[N-[(1,1-dimethylethoxy)carbonyl]-3-[(triphenylmethyl)thio]-D-valyl]glycine, methyl ester

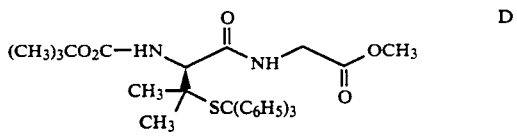

To a stirred solution of $N^\alpha$-Boc-S-trityl-D-penicillamine (19.7 g, 0.04 mol) in 140 mL of DMF cooled to 5° C. was added 5.1 g (0.04 mol) of methyl glycinate hydrochloride, 5.4 g (0.04 mol) of 1-hydroxybenzotriazole hydrate, 8.1 g (0.042 mol) of 1-(3-dimethylaminopropyl)3-ethylcarbodiimide hydrochloride, and 9.1 mL (0.082 mol) of N-methylmorpholine. The reaction was allowed to warm to room temperature and stirred over night. It was then diluted with 500 mL of EtOAc and washed with 3×500 mL of 0.5N KHSO₄, 2×500 mL of saturated KHCO₃ solution and 2 x 500 mL of brine. The organic layer was dried over anhydrous Na₂SO₄ before all solvent was removed under reduced pressure. The yield of the fairly pure white solid title product was 22.2 g (99%), and was used without further purification.

EXAMPLE 33

N-[N-[(1,1-dimethylethoxy)carbonyl]-3-[(triphenylmethyl)thio]-D-valyl]glycine

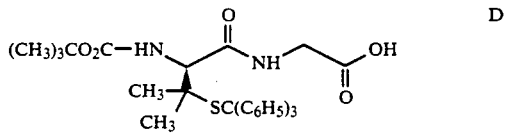

To a MeOH (160 mL) solution of the product of Example 32 (22.2 g, 0.039 mol) was added dropwise to vigorously-stirred 80 mL of 1.0 N NaOH. After 2 hours, the pH of the homogenous solution was adjusted to pH 2 with 1.0 M KHSO₄. The white precipitate generated was filtered, washed with water, dried in the vacuum oven at 50° C. over night and dissolved in 150 mL of CH₂Cl₂. This solution was filtered before the solvent volume was reduced by rotary evaporation, and the product precipitated with n-hexane. The white solid product was filtered, washed with hexane, and dried in vacuo. A crude 24.8 g (98% by HPLC) sample of the desired title material was isolated as a white solid, and was used without further purification.

EXAMPLE 34

4-chloro-N-[N-[N-[(1,1-dimethylethoxy)carbonyl]-3-[(triphenylmethyl)thio]-D-valyl]glycyl]-L-phenylalanine, methyl ester The product of Example 33 (9.2 g, 16.7 mmol) was coupled with N$^\alpha$-Boc-p-chloro-L-phenylalanine (4.3 g, 16 7 mmol) by the method described above in Example 32. A 12.5 g (94% by HPLC) sample of the desired title material was isolated as a white solid, and was used without further purification.

EXAMPLE 35

4-chloro-N-[N-[N-[(1,1-dimethylethoxy)carbonyl]-3-[(triphenylmethyl)thio]-D-valyl]glycyl]-L-phenylalanine The title product was synthesized from the title material synthesized in Example 34 (12.5 g, 16.0 mmol) by the method described above in Example 33. An 11.2 g (92%) sample of the desired title compound was isolated as a white solid, and was used in Example 36 without further purification.

EXAMPLE 36

4-chloro-N-[N-[N-[(1,1-dimethylethoxy)carbonyl]-3-](triphenylmethyl)thio]-D-valyl]glycyl]-DL-phenylalanyl]-3-](triphenylmethyl)thio]-D-valine

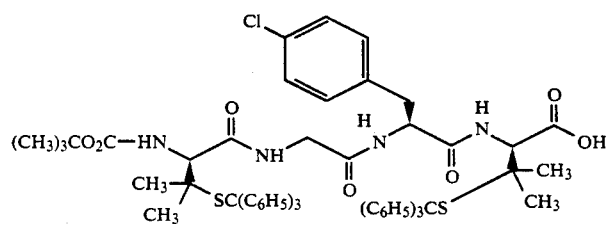
D,L,D

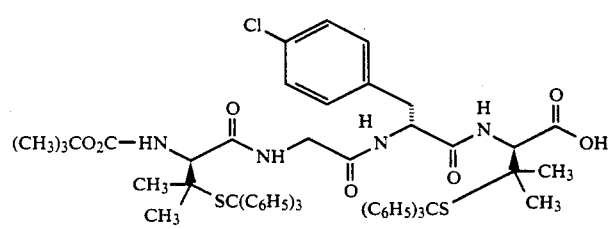
D,D,D

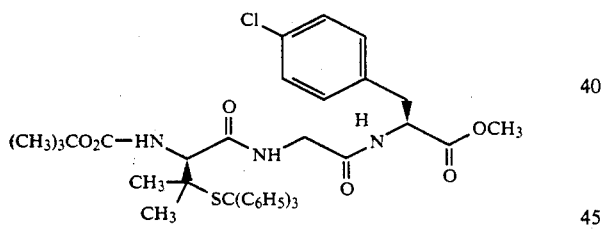
D,L

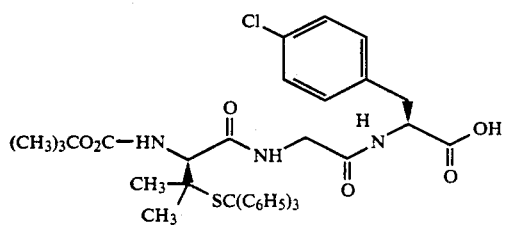
D,L

The product of Example 35 (11.6 g, 15.8 mmol) was coupled to S-trityl-D-penicillamine (6.5 g, 16.7 mmol) by the method described above in Example 32. Racemization at the p-chlorophenylalanine residue took place during the coupling. Both title diastereomers were isolated by flash chromatography on an 80×200 mm column of EM Silica Gel 60 eluting with a mixture of CH$_2$Cl$_2$/ETOH/HOAc (94.8/5.0/0.2). A 2.75 g (94% pure by HPLC) sample of the A-diastereomer title compound and a 3.6 g (91% pure by HPLC) sample of the B-diastereomer title compound were isolated as a white solids.

Diastereomer - A:
 NMR (QE-300) shift of (pCl)Phe$^3$, C—H (CDCl$_3$)=4.48–4.58 δ.
Diastereomer - B:
 NMR (QE-300) shift of (pCl)Phe$^3$, C—H (CDCl$_3$)=4.64–4.75 δ.

EXAMPLE 37

4-chloro-N-[N-[N-[(1,1-dimethylethoxy)carbonyl]-3-[(triphenylmethyl)thio]-D-valyl]glycyl]phenylalanyl]-3-[(triphenylmethyl)thio]-D-valine, phenylmethyl ester

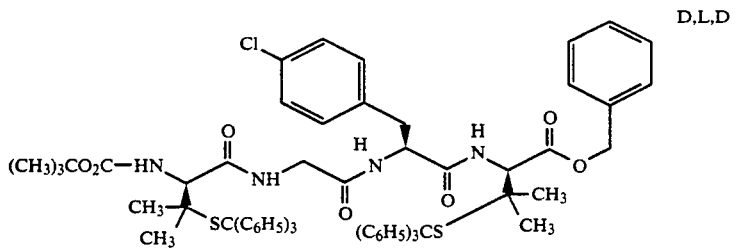

D,L,D

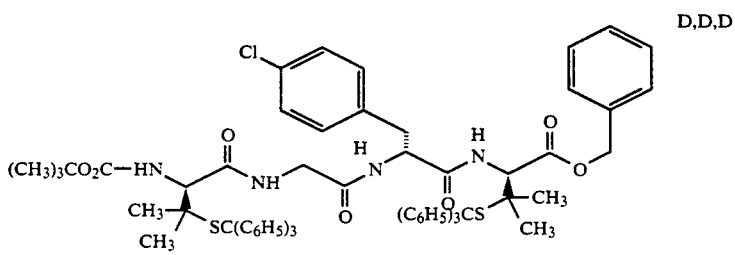

D,D,D

A solution of 2.2 g (2.05 mmol) of the B-diastereomer product synthesized in Example 36 in 40 mL of MeOH was titrated with a 20% $Cs_2CO_3$ solution to pH 7, and stripped of all solvent under reduced pressure. The residue was twice dissolved in 15 mL of DMF and stripped of all solvent. The dry salt was dissolved in 25 mL of DMF, and 0.39 g (2.2 mmol)-of benzyl bromide were added. The reaction was stirred over night at room temperature. After filtering off the precipitated CsBr, all solvent was removed in vacuo from the filtrate. The residue was treated with 100 mL of water, filtered and washed with water before it was dissolved in 50 mL of EtOAc. This solution was washed with 30 mL of brine, dried over anhydrous $Na_2SO_4$, and stripped of all solvent under vacuum to yield 2.5 g (71%) of the title compound, which was used in Example 38 without further purification.

EXAMPLE 38

N-[(1,1-dimethylethoxy)carbonyl]-3-mercapto-D-valylglycyl-4-chlorophenylalanyl-3-mercapto-D-valine, cyclic (2→5)-disulfide, phenylmethyl ester

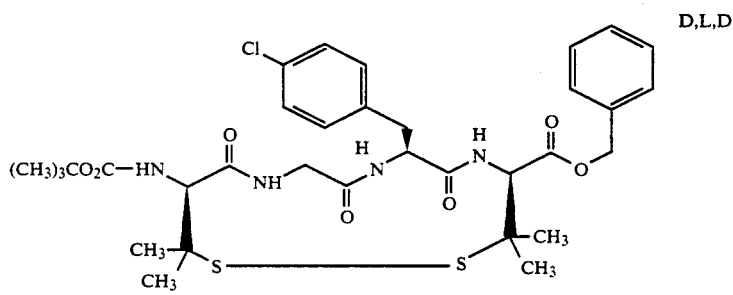

D,L,D

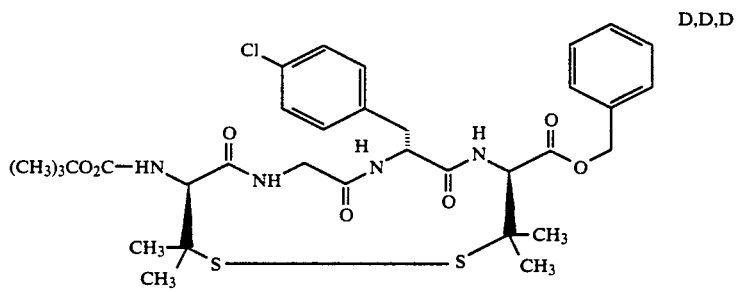

D,D,D

The title compound of Example 37 (2.2 g, 1.9 mmol) was converted to the title compound of this example by the method described above in Example 29. The 2.9 g of crude product was submitted to flash column separation on a 40×200 mm column of EM Silica Gel 60 eluting with 100% $CH_2Cl_2$ to $CH_2Cl_2$/EtOAc (1/1). A 0.47 g (36%) sample of the desired title compound was isolated as a white solid.

EXAMPLE 39

3-mercapto-D-valylglycyl-4-chlorophenylalanyl-3-mercapto-D-valine, cyclic (2→5)-disulfide, phenylmethyl ester, monohydrochloride

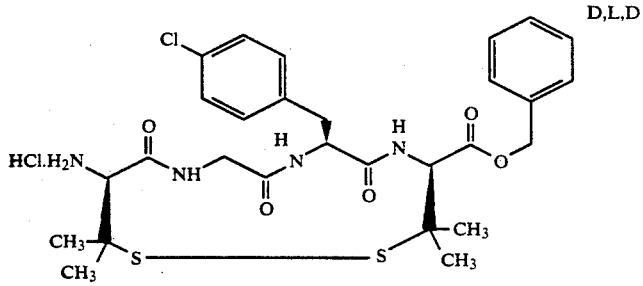

D,L,D

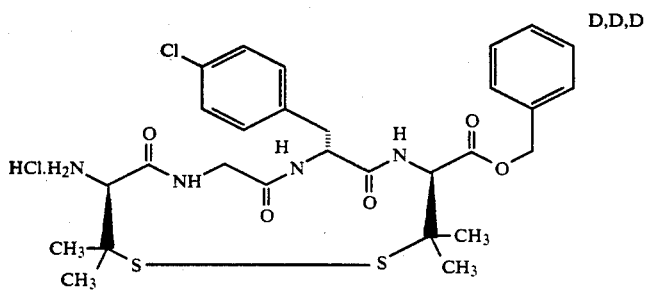

D,D,D

To 0.47 g (0.7 mmol) of the product synthesized in Example 38 in 20 mL of HOAc was added 2 mL of 6.8 N HCl/dioxane. After 40 minutes, the reaction was filtered and stripped of all solvent in vacuo. The residue was triturated with Et₂O, filtered and washed with Et₂O to yield 0.45 g (99%) of the white solid title product.

EXAMPLE 40

N-[(1,1-dimethylethoxy)carbonyl]-2,6-dimethyl-L-tyrosyl-3-mercapto-D-valylglycyl-4-chloro-L-phenylalanyl-3-mercapto-D-valine, cyclic (2→5)-disulfide, phenylmethyl ester N$^\alpha$-Boc-2,6-dimethyl-L-tyrosine (0.34 g, 1.1 mmol) was coupled to the product of Example 39 (0.6 g, 0.96 mmol) by the method described above in Example 28. A 0.41 g (48%) sample of the desired title material was isolated as a white solid after flash column chromatography on EM silica gel eluting with a mixture of EtOAc/n-hexane/HOAc (69.9/30/0.1).

Analysis Calculated for $C_{44}H_{56}N_5O_9S_2Cl$ (MW=898.50): C, 58.81; H, 6.28; N, 7.79; S, 7.14. Found: C, 58.91; H, 6.36; N, 7.35; S, 6.69.

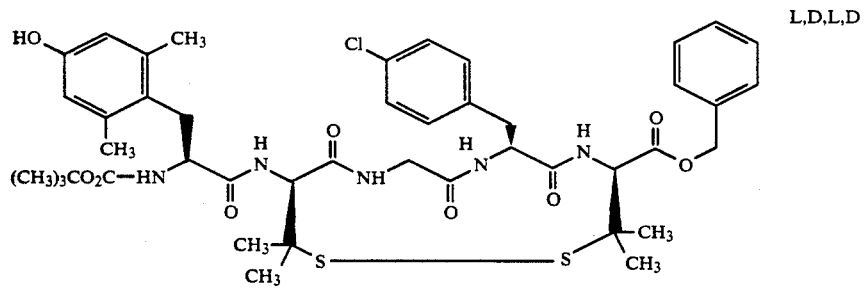

L,D,L,D

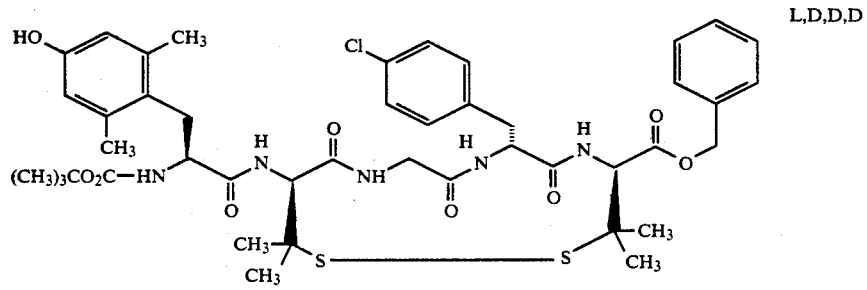

L,D,D,D

EXAMPLE 41

2.6-dimethyl-L-tyrosyl-3-mercapto-D-valylglycyl-4-chloro-L-phenylalanyl-3-mercapto-D-valine, cyclic (2→5)-disulfide, phenylmethyl ester, monohydrochloride

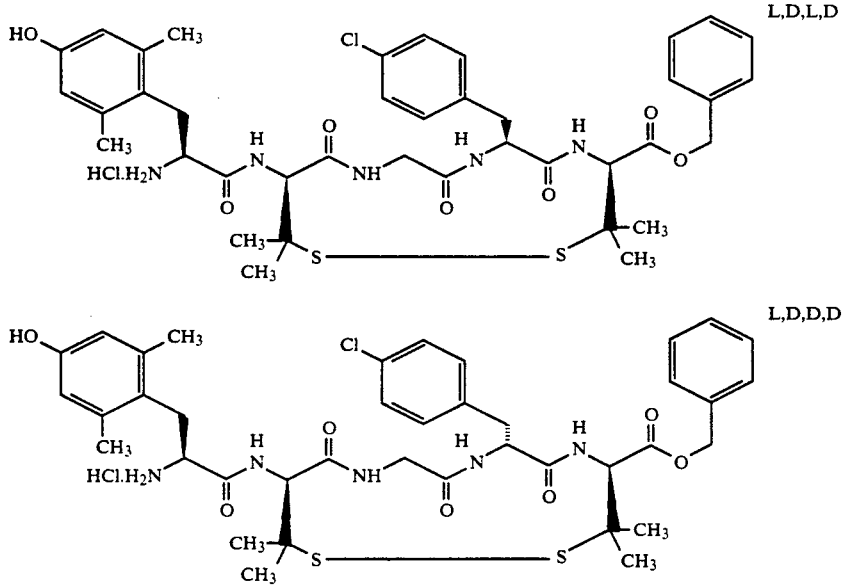

The title product of Example 40 (0.41 g, 0.46 mmol) was converted to the title compound by the method described above in Example 39. A 0.31 g (74%) sample of the desired title compound was isolated as a white solid salt.

Analysis Calculated for $C_{39}H_{48}N_5O_7S_2Cl + 1.0$ HCl (MW = 834.85): C, 56.10; H, 5.92; N, 8.39; S, 7.68; Cl, 8.49. Found: C, 55.72; H, 6.03; N, 8.03; S, 7.14; Cl, 8.46.

EXAMPLE 42

2,6-Dimethyl-L-tyrosyl-3-mercapto-D-valyl-L-glycyl-N-methyl-2-thiphenylalaninyl-3-mercapto-D-valine, cyclic (2→5)-disulfide

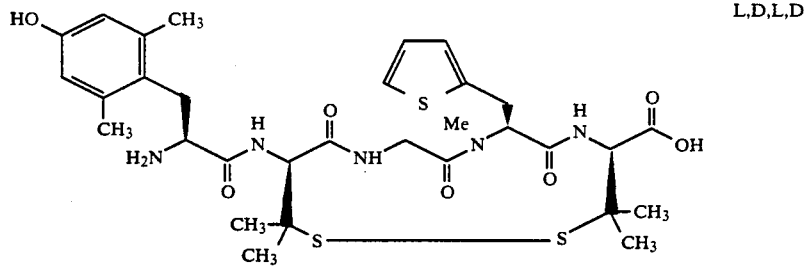

The title product is synthesized by the method of Example 4 wherein Boc-N-methyl-2-thiophenylalanine replaces Boc-L-phenylalanine[4] in the synthetic sequence.

The foregoing examples are provided to enable one of ordinary skill in the art to practice the present invention. These examples are merely illustrative, however, and should not be read as limiting the scope of the invention as it is claimed in the appended claims.

While the invention has been described and illustrated with reference to certain prepared embodiments thereof, those skilled in the art will appreciate that various changes, modifications and substitutions can be made therein without departing from the spirit and scope of the invention. For example, effective dosages other than the preferred range as set forth herein above may be applicable as a consequence of variations in the responsiveness of the animal being treated to induce analgesia, dosage-related adverse effects, if any, and analogous considerations. Likewise, the specific pharmacological responses observed may vary according to, and depending upon, the particular active compound selected, or whether there are present certain pharmaceutical carriers, as well as the type of formulation and mode of administration employed, and such expected variations or differences in the results are contemplated in accordance with the objects and practices of the present invention. It is intended therefore that the invention be limited only by the scope of the claims which follow, and that such claims be interpreted as broadly as is reasonable.

What is claimed is:
1. A compound having the structure:

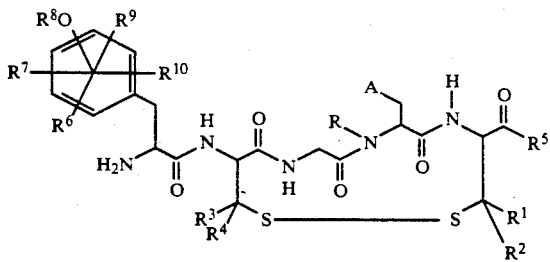

and the pharmaceutically-acceptable salts, esters and amides thereof, wherein:

A is: hydrogen,

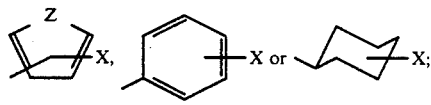

Z is: sulfur, nitrogen or oxygen;

X is: hydrogen, halogen, nitro, lower alkyl, lower alkyl substituted by halogen or nitro, aralkyl, alkaryl, or aralkyl or alkaryl substituted by hydrogen, halogen, nitro, lower alkyl or lower alkyl substituted by halogen or nitro;

R, $R^1$, $R^2$, $R^3$, $R^4$, $R^6$, $R^7$, $R^9$ and $R^{10}$ are: independently hydrogen or alkyl, with the proviso that $R^6$, $R^7$, $R^9$ and $R^{10}$ are not each hydrogen;

$R^5$ is: amino, hydroxy, alkoxy, alkylamino, dialkylamino or alkoxyaryl; and $R^8$ is: hydrogen, alkyl, alkyl carbonyl, alkoxy carbonyl, amino carbonyl, alkylaminocarbonyl or dialkylamino carbonyl, with any of the foregoing $R^8$ substituents being aryl substituted.

2. A compound of claim 1 wherein A is

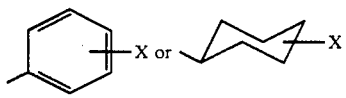

and X is hydrogen or halogen.

3. A compound of claim 2 wherein $R^1$, $R^2$, $R^3$ and $R^4$ are each independently hydrogen or methyl.

4. A compound of claim 3 wherein $R^8$ is hydrogen, lower alkyl, alkyl carbonyl, alkoxy carbonyl or alkylaminocarbonyl.

5. A compound of claim 4 wherein $R^8$ is hydrogen, methyl, methyl carbonyl, lower alkoxy carbonyl or aminocarbonyl.

6. A compound of claim 5 wherein $R^6$, $R^7$, $R^9$ and $R^{10}$ are each independently hydrogen or lower alkyl.

7. A compound of claim 6 wherein $R^6$, $R^7$, $R^9$ and $R^{10}$ are each independently hydrogen or methyl.

8. A compound of claim 7 wherein R is hydrogen.

9. A compound of claim 8 wherein two of $R^6$, $R^7$, $R^9$ and $R^{11}$ are hydrogen and two of $R^6$, $R^7$, $R^9$ and $R^{10}$ are methyl.

10. A compound of claim 8 wherein one of $R^6$, $R^7$, $R^9$ and $R^{10}$ is hydrogen and the rest of $R^6$, $R^7$, $R^9$ and $R^{10}$ are each methyl.

11. A compound of claim 8 wherein one of $R^6$, $R^7$, $R^9$ and $R^{10}$ is methyl and the rest of $R^6$, $R^7$, $R^9$ and $R^{10}$ are each hydrogen.

12. A compound of claim 8 wherein A is

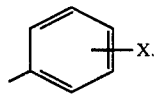

13. A compound of claim 12 wherein $R^8$ is hydrogen, methyl, methoxy, —COOCH$_2$CH$_2$CH$_3$ or —CONHCH$_3$.

14. A compound of claim 13 wherein $R^5$ is hydroxy, methoxy, —NH$_2$ or —NHCH$_2$CH$_3$.

15. A compound of claim 1 wherein the compound is:

2,6-dimethyl-L-tyrosyl-3-mercapto-D-valylglycyl-L-phenylalanyl-3-mercapto-D-valine, cyclic (2→5)-disulfide;

2,6-dimethyl-L-tyrosyl-3-mercapto-D-valylglycyl-L-phenylalanyl-3-mercapto-L-valine, cyclic (2→5)-disulfide;

2,6-dimethyl-L-tyrosyl-3-mercapto-D-valylglycyl-4-fluoro-L-phenylalanyl-3-mercapto-D-valine, cyclic (2→5)-disulfide;

2,6-dimethyl-L-tyrosyl-3-mercapto-D-valylglycyl-L-phenylalanyl-3-mercapto-D-valinamide, cyclic (2→5)-disulfide;

2,6-dimethyl-L-tyrosyl-3-mercapto-D-valylglycyl-L-phenylalanyl-3-mercapto-D-valine, cyclic (2→5)-disulfide, methyl ester;

2,3,6-trimethyl-L-tyrosyl-3-mercapto-D-valylglycyl-L-phenylalanyl-3-mercapto-D-valine, cyclic (2→5) disulfide;

3-hydroxy-2,4-dimethyl-L-phenylalanyl-3-mercapto-D-valylglycyl-L-phenylalanyl-3-mercapto-D-valine, cyclic (2→5)-disulfide;

2,6-dimethyl-L-tyrosyl-3-mercapto-D-valylglycyl-4-chloro-L-phenylalanyl-3-mercapto-D-valinamide, cyclic (2→5)-disulfide;

2,6-dimethyl-L-tyrosyl-3-mercapto-D-valylglycyl-4-fluoro-L-phenylalanyl-3-mercapto-D-valinamide, cyclic (2→5)-disulfide;

2,6-dimethyl-L-tyrosyl-3-mercapto-D-valylglycyl-3-cyclohexyl-L-alanyl-3-mercapto-D-valinamide, cyclic (2→5)-disulfide; or 2,6-dimethyl-L-tyrosyl-3-mercapto-D-valylglycyl-4-chloro-L-phenylalanyl-3-mercapto-D-valine, cyclic (2→5)-disulfide, phenylmethyl ester, monohydrochloride.

16. A compound of claim 15 wherein the compound is:

2,6-dimethyl-L-tyrosyl-3-mercapto-D-valylglycyl-L-phenylalanyl-3-mercapto-D-valine, cyclic (2→5)-disulfide;

2,6-dimethyl-L-tyrosyl-3-mercapto-D-valylglycyl-L-phenylalanyl-3-mercapto-D-valinamide, cyclic (2→5)-disulfide;

2,6-dimethyl-L-tyrosyl-3-mercapto-D-valylglycyl-L-phenylalanyl-3-mercapto-D-valine, cyclic (2→5)-disulfide, methyl ester;

2,3,6-trimethyl-L-tyrosyl-3-mercapto-D-valylglycyl-L-phenylalanyl-3-mercapto-D-valine, cyclic (2→5) disulfide;

2,6-dimethyl-L-tyrosyl-3-mercapto-D-valylglycyl-4-fluoro-L-phenylalanyl-3-mercapto-D-valinamide, cyclic (2→5)-disulfide;

2,6-dimethyl-L-tyrosyl-3-mercapto-D-valylglycyl-3-cyclohexyl-L-alanyl-3-mercapto-D-valinamide, cyclic (2→5)-disulfide; or 2,6-dimethyl-L-tyrosyl-3-mercapto-D-valylglycyl-4-chloro-L-phenylalanyl-3-mercapto-D-valine, cyclic (2→5)-disulfide, phenylmethyl ester, monohydrochloride.

17. A compound of claim 16 wherein the compound is:

2,6-dimethyl-L-tyrosyl-3-mercapto-D-valylglycyl-L-phenylalanyl-3-mercapto-D-valine, cyclic (2→5)-disulfide;

2,6-dimethyl-L-tyrosyl-3-mercapto-D-valylglycyl-L-phenylalanyl-3-mercapto-D-valinamide, cyclic (2→5)-disulfide;

2,6-dimethyl-L-tyrosyl-3-mercapto-D-valylglycyl-L-phenylalanyl-3-mercapto-D-valine, cyclic (2→5)-disulfide, methyl ester; or 2,6-dimethyl-L-tyrosyl-3-mercapto-D-valylglycyl-4-fluoro-L-phenylalanyl-3-mercapto-D-valinamide, cyclic (2→5)-disulfide.

18. A compound of claim 1, having the structure:

L,D,L,D

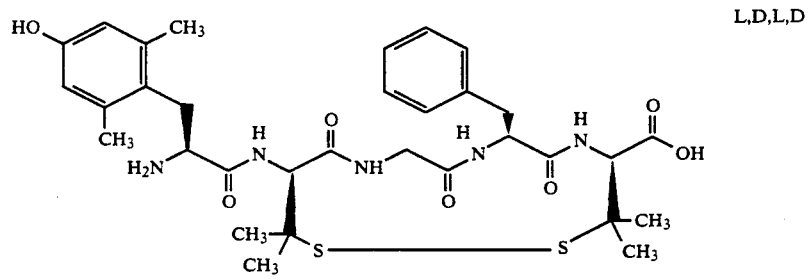

19. A compound of claim 1, having the structure:

L,D,L,D

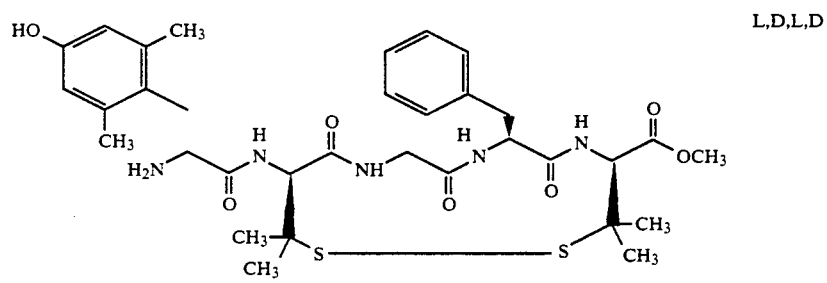

20. A compound of claim 1, having the structure:

L,D,L,D

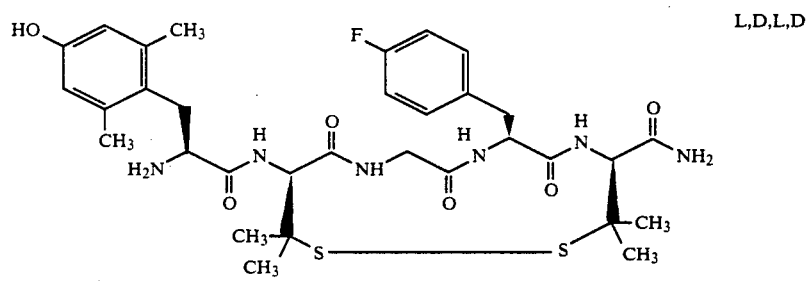

21. A compound of claim 1, having the structure:

L,D,L,D

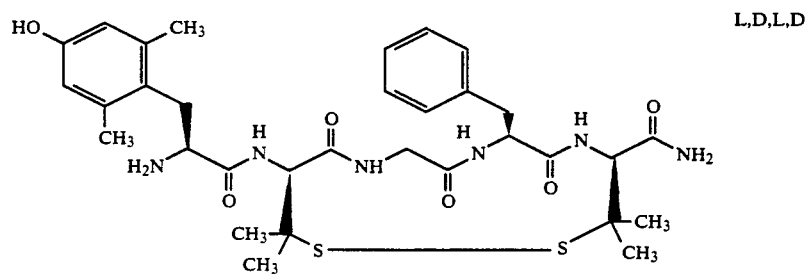

22. A compound of claim 1, having the structure:

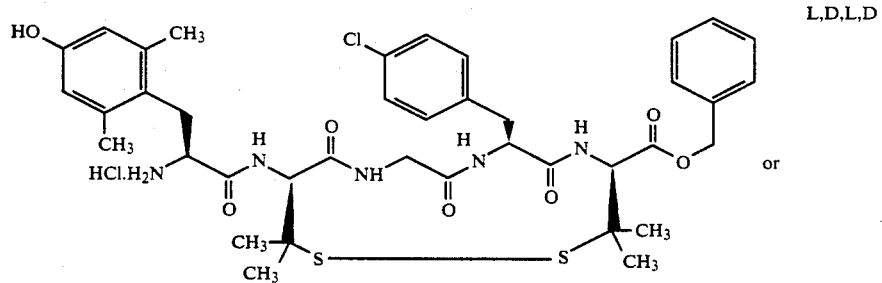

L,D,L,D or

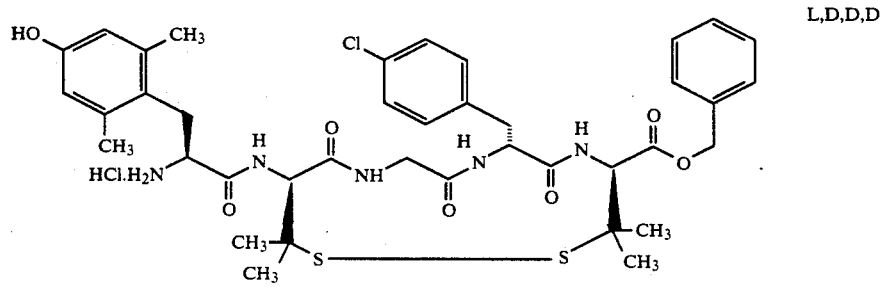

L,D,D,D

23. A compound of claim 1, having the structure:

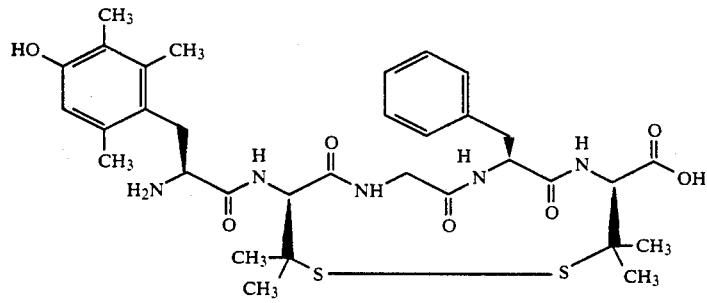

24. A compound of claim 1, having the structure:

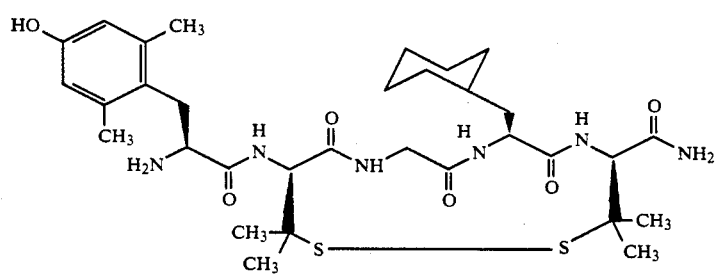

25. A pharmaceutical composition comprising a pharmaceutically-acceptable carrier and a compound of claim 1.

26. The pharmaceutical composition of claim 25 wherein the compound is:

2,6-dimethyl-L-tyrosyl-3-mercapto-D-valylglycyl-L-phenylalanyl-3-mercapto-D-valine, cyclic (2→5)-disulfide;

2,6-dimethyl-L-tyrosyl-3-mercapto-D-valylglycyl-L-phenylalanyl-3-mercapto-D-valinamide, cyclic (2→5)-disulfide;

2,6-dimethyl-L-tyrosyl-3-mercapto-D-valylglycyl-L-phenylalanyl-3-mercapto-D-valine, cyclic (2→5)-disulfide, methyl ester; or 2,6-dimethyl-L-tyrosyl-3-mercapto-D-valylglycyl-4-

L,D,L,D fluoro-L-phenylalanyl-3-mercapto-D-valinamide,

L,D,L,D cyclic (2→5)-disulfide.

27. A method for treating pain in an animal comprising administering to said animal a therapeutically-effective amount of a compound of claim 1, said compound exhibiting activity systemically.

28. The method of claim 27 wherein the compound is:

2,6-dimethyl-L-tyrosyl-3-mercapto-D-valylglycyl-L-phenylalanyl-3-mercapto-D-valine, cyclic (2→5)-disulfide;

2,6-dimethyl-L-tyrosyl-3-mercapto-D-valylglycyl-L-phenylalanyl-3-mercapto-D-valinamide, cyclic (2→5)-disulfide;

2,6-dimethyl-L-tyrosyl-3-mercapto-D-valylglycyl-L-phenylalanyl-3-mercapto-D-valine, cyclic (2→5)-disulfide, methyl ester; or 2,6-dimethyl-L-tyrosyl-3-mercapto-D-valylglycyl-4-fluoro-L-phenylalanyl-3-mercapto D valinamide, cyclic (2→5)-disulfide.

* * * * *

UNITED STATES PATENT AND TRADEMARK OFFICE
CERTIFICATE OF CORRECTION

PATENT NO. : 5,169,833

DATED : December 8, 1992

INVENTOR(S) : Hansen, Jr., et al.

It is certified that error appears in the above-identified patent and that said Letters Patent is hereby corrected as shown below:

Abstract reading, "slats" should read -- salts --.

Column 2, line 4, reading "(I)" should read -- (1) --.

Column 3, line 18, reading "D-Pens$^5$" should read -- D-Pen$^5$ --.

Column 4, line 55, reading "Definitions" should read -- (1) Definitions --.

Column 5, line 9, reading "by-an" should read -- by an --.

Column 9, line 33, reading "Description of Invention" should read -- (2) Description of Invention --.

Column 9, line 61, reading "d-isomers, isomers," should read -- $\underline{d}$-isomers, $\underline{l}$-isomers, --.

Column 10, line 59, reading "Utility" should read -- (3) Utility --.

Column 10, line 66, reading "Methods of Preparation" should read -- (4) Methods of Preparation --.

Column 22, line 47, reading "Dosage and Mode of Administration" should read -- (5) Dosage and Mode of Administration --.

Column 28, line 18, reading "Examples" should read -- (6) Examples --.

Column 29, line 48, reading "Which" should read -- which --.

UNITED STATES PATENT AND TRADEMARK OFFICE
CERTIFICATE OF CORRECTION

PATENT NO. : 5,169,833

DATED : December 8, 1992

INVENTOR(S) : Hansen, Jr., et al.

It is certified that error appears in the above-identified patent and that said Letters Patent is hereby corrected as shown below:

Column 30, line 25, reading "0.1 ml" should read -- 0.1 mL --.

Column 30, line 68, reading "26)" should read -- 16) --.

Column 31, line 56, reading "*PharmacoI.*" should read -- *Pharmacol.* --.

Column 33, line 45, reading "TrisHCl" should read -- Tris/HCl --.

Column 42, line 30, reading structure

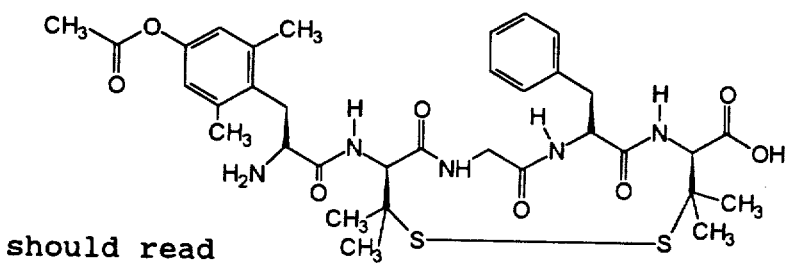

should read

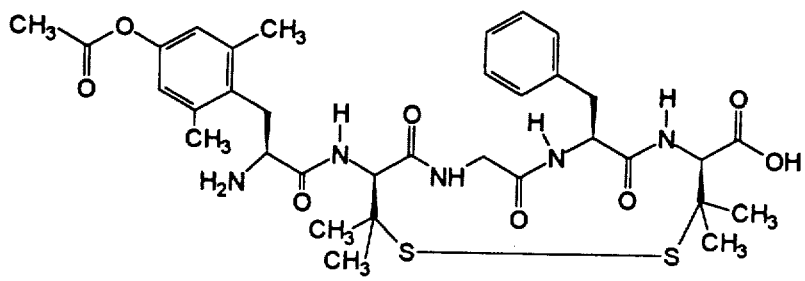

UNITED STATES PATENT AND TRADEMARK OFFICE
CERTIFICATE OF CORRECTION

PATENT NO. : 5,169,833
DATED : December 8, 1992
INVENTOR(S) : Hansen, Jr., et al.

It is certified that error appears in the above-identified patent and that said Letters Patent is hereby corrected as shown below:

Column 42, line 60, reading structure

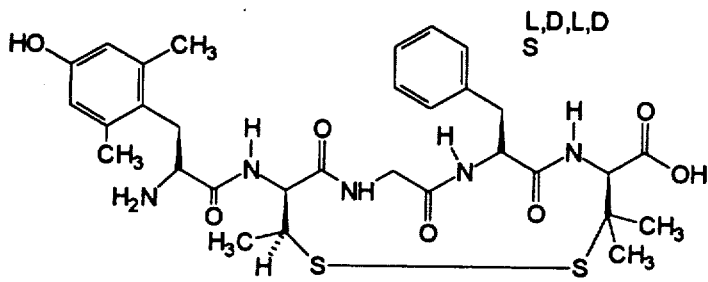

should read

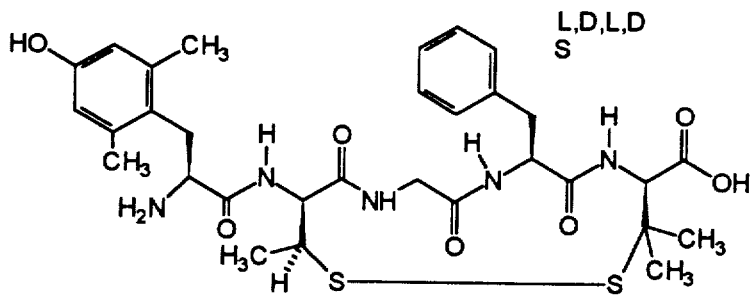

Column 44, line 47, reading "H 6.36;" should read -- H, 6.36; --.

Column 45, line 43, reading "white solid" should read -- white solid salt. --.

Column 48, line 30, reading "218TpS4," should read -- 218TPS4, --.

UNITED STATES PATENT AND TRADEMARK OFFICE
CERTIFICATE OF CORRECTION

PATENT NO. : 5,169,833

DATED : December 8, 1992

INVENTOR(S) : Hansen, Jr., et al.

It is certified that error appears in the above-identified patent and that said Letters Patent is hereby corrected as shown below:

Column 48, line 32, reading "(01.%" should read -- (0.1% --.

Column 49, line 63, reading "retention" should read -- retention time. --.

Column 50, line 64, reading "A mg" should read -- A 35 mg --.

Column 50, line 68, reading "S," should read -- S, 6.55. --.

Column 51, line 18, reading "of 5" should read -- of Example 15 --.

Column 54, line 28, reading "in vacuo." should read -- in vacuo, --.

Column 54, line 29, reading "I x 0.5" should read -- 1 x 0.5 --.

Column 54, line 33, reading "mL d" should read -- mL saturated --.

Column 55, line 1, reading "and-all" should read -- and all --.

Column 55, line 6, reading "I6" should read -- 16 --.

Column 58, line 2, reading "I6.0" should read -- 16.0 --.

Column 58, line 60, reading "(9I%" should read -- (91% --.

Column 59, line 60, reading "mmol)-of" should read -- mmol) of --.

Column 60, line 66, reading "(I/1)." should read -- (1/1). --.

UNITED STATES PATENT AND TRADEMARK OFFICE
CERTIFICATE OF CORRECTION

PATENT NO. : 5,169,833
DATED : December 8, 1992
INVENTOR(S) : Hansen, Jr., et al.

It is certified that error appears in the above-identified patent and that said Letters Patent is hereby corrected as shown below:

Column 68, line 25, reading structure in claim 19

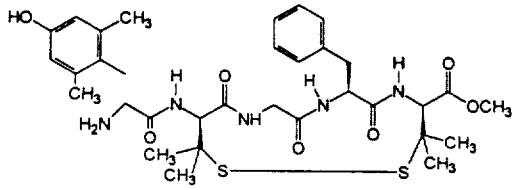

should read

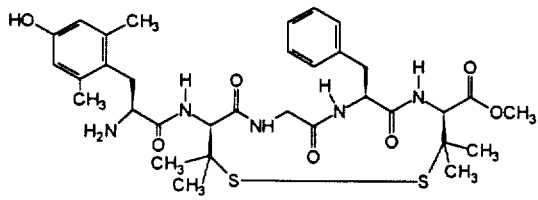

Signed and Sealed this

Twenty-first Day of June, 1994

Attest:

BRUCE LEHMAN

Attesting Officer    Commissioner of Patents and Trademarks